(12) United States Patent
Miller et al.

(10) Patent No.: US 10,028,894 B2
(45) Date of Patent: Jul. 24, 2018

(54) DENTAL COMPOSITION CONTAINING POLYOXOMETALATES, PROCESS OF PRODUCTION AND USE THEREOF

(71) Applicant: 3M INNOVATIVE PROPERTIES COMPANY, St. Paul, MN (US)

(72) Inventors: Adam D. Miller, St. Paul, MN (US); Matthew H. Frey, Cottage Grove, MN (US); Timothy D. Dunbar, Woodbury, MN (US); Henry Loll, Gilching (DE); Christoph Thalacker, Weilheim (DE)

(73) Assignee: 3M Innovative Properties Company, St. Paul, MN (US)

( * ) Notice: Subject to any disclaimer, the term of this patent is extended or adjusted under 35 U.S.C. 154(b) by 55 days.

(21) Appl. No.: 14/917,047

(22) PCT Filed: Sep. 4, 2014

(86) PCT No.: PCT/US2014/053977
§ 371 (c)(1),
(2) Date: Mar. 7, 2016

(87) PCT Pub. No.: WO2015/034977
PCT Pub. Date: Mar. 12, 2015

(65) Prior Publication Data
US 2016/0199267 A1    Jul. 14, 2016

(30) Foreign Application Priority Data
Sep. 9, 2013    (EP) .................................... 13183526

(51) Int. Cl.
*A61K 6/083*    (2006.01)
*A61K 6/087*    (2006.01)
*A61K 6/00*    (2006.01)

(52) U.S. Cl.
CPC ............ *A61K 6/087* (2013.01); *A61K 6/0023* (2013.01); *A61K 6/0073* (2013.01); *A61K 6/083* (2013.01)

(58) Field of Classification Search
CPC .................................................... A61K 6/083
See application file for complete search history.

(56) References Cited

U.S. PATENT DOCUMENTS

| | | |
|---|---|---|
| 3,729,313 A | 4/1973 | Smith |
| 3,741,769 A | 6/1973 | Smith |
| 3,808,006 A | 4/1974 | Smith |
| 4,071,424 A | 1/1978 | Dart |
| 4,250,053 A | 2/1981 | Smith |
| 4,259,075 A | 3/1981 | Yamauchi |
| 4,394,403 A | 7/1983 | Smith |
| 4,499,251 A | 2/1985 | Omura |
| 4,537,940 A | 8/1985 | Omura |
| 4,539,382 A | 9/1985 | Omura |
| 4,642,126 A | 2/1987 | Zador |
| 4,652,274 A | 3/1987 | Boettcher |
| 4,737,593 A | 4/1988 | Ellrich |
| 4,772,530 A | 9/1988 | Gottschalk |
| 4,872,936 A | 10/1989 | Engelbrecht |
| 4,874,450 A | 10/1989 | Gottschalk |
| 4,954,414 A | 9/1990 | Adair |
| 5,055,372 A | 10/1991 | Shanklin |
| 5,057,393 A | 10/1991 | Shanklin |
| 5,130,347 A | 7/1992 | Mitra |
| 5,178,989 A | 1/1993 | Heller |
| 5,530,038 A | 6/1996 | Yamamoto |
| 5,545,676 A | 8/1996 | Palazzotto |
| 5,548,052 A | 8/1996 | Katsoulis |
| 5,624,260 A | 4/1997 | Wilcox |
| 5,865,803 A | 2/1999 | Major |
| 5,893,714 A | 4/1999 | Arnold |
| 5,918,772 A | 7/1999 | Keller |
| 5,944,419 A | 8/1999 | Streiff |
| 6,105,761 A | 8/2000 | Peuker |
| 6,324,916 B1 | 12/2001 | Jessop |
| 6,444,725 B1 | 9/2002 | Trom |
| 6,458,868 B1 | 10/2002 | Okada |
| 6,572,693 B1 | 6/2003 | Wu |
| 2003/0004294 A1 | 1/2003 | Moszner |
| 2005/0236586 A1 | 10/2005 | Hartung |
| 2006/0187752 A1 | 8/2006 | Keller |
| 2007/0090079 A1 | 4/2007 | Kelller |
| 2007/0166588 A1* | 7/2007 | Kanaoka ................ C08J 5/2256 |
| | | 429/483 |
| 2007/0172789 A1 | 7/2007 | Muller |
| 2009/0208809 A1* | 8/2009 | Hamrock ............ H01M 8/1023 |
| | | 429/492 |
| 2010/0041789 A1 | 2/2010 | Neffgen |

(Continued)

FOREIGN PATENT DOCUMENTS

| | | |
|---|---|---|
| EP | 0712622 | 5/1996 |
| EP | 0944364 | 9/1999 |
| EP | 1051961 | 11/2000 |
| EP | 1340472 | 9/2003 |
| WO | WO 2000-69392 | 11/2000 |
| WO | WO 2006-060033 | 6/2006 |
| WO | WO 2009-151957 | 12/2009 |
| WO | WO 2011-056814 | 5/2011 |
| WO | WO 2012-064573 | 5/2012 |

OTHER PUBLICATIONS

Judeinstein, "Synthesis and Properties of Polyoxometalates Based Inorganic-Organic Polymers", Chem. Mater., 1992, vol. 4, pp. 4-7.
Knoth, "Derivatives of Heteropolyanions 1. Organic Derivatives of $W_{12}SiO_{40}^{4-}$, $W_{12}PO_{40}^{3-}$, and $Mo_{12}SiO_{40}^{4-}$", Journal of the American Chemical Society, Jan. 31, 1979, vol. 100, pp. 759-760.
Pope, "Polyoxometalates", Encyclopedia of Inorganic and Bioinorganic Chemistry, 2006, pp. 1-11.

(Continued)

*Primary Examiner* — Michael Pepitone

(57) ABSTRACT

The invention relates to a curable composition for dental use comprising polyoxymetalates and/or derivatives thereof in an amount of at least about 5 wt.-% with respect to the weight of the composition.

11 Claims, No Drawings

(56) References Cited

U.S. PATENT DOCUMENTS

2010/0068593 A1* 3/2010 Reiche ................ H01M 8/1023
  429/463
2010/0241071 A1  9/2010  Atanasoska
2011/0009586 A1  1/2011  Matsuda

OTHER PUBLICATIONS

Teze, "α-, β-, and γ-Dodecatungstosilicic Acids: Isomers and Related Lacunary Compounds", Inorganic Syntheses, 1990, vol. 27, pp. 85-96.
International Search Report for PCT International Application No. PCT/US2014/053977 dated Nov. 20, 2014, 4 pages.

* cited by examiner

DENTAL COMPOSITION CONTAINING POLYOXOMETALATES, PROCESS OF PRODUCTION AND USE THEREOF

CROSS-REFERENCE TO RELATED APPLICATIONS

This application is the § 371 U.S. National Stage of International Application No. PCT/US2014/053977, filed Sep. 4, 2014, which claims the benefit of EP 13183526.6, filed Sep. 9, 2013.

FIELD OF THE INVENTION

The invention relates to dental compositions containing polyoxometalates, process of production and use thereof.

BACKGROUND ART

Dental materials which are designed to remain in the mouth of a patient are often radiopaque which enables the practitioner to identify them on an x-ray film. This is of particular importance if the dental material is highly aesthetic and thus cannot be easily distinguished from natural tooth structure.

Radiopacity is typically imparted to a dental material by incorporation of an inorganic filler containing heavy metal elements. Examples of radiopaque fillers used in dentistry include ground glasses containing heavy metal elements such as strontium or barium, various metal oxide nanoparticles (e.g. zirconia also referred to as nano-zirconia) which can either be used as discrete particles, or as clusters of particles together with, e.g. silica particles, and insoluble salts of heavier rare earths, such as yttrium fluoride or ytterbium fluoride.

For several reasons, however, it is often desirable to have small-sized radiopaque additives (e.g., on the nanometer scale) for use in dental materials:
  for more highly viscous materials such as filling composites and luting cements, it is desirable to have small additives to fill in the gaps between larger filler particles in order to achieve high filler loading and high mechanical strength;
  for lower viscous materials, such as adhesives or sealants, small additives are desired to prevent settling of the filler out of the liquid, and thus maintain a homogeneous material throughout its shelf life; and
  for all aesthetic dental materials, small additives with a size below the wavelength of visible light are desired, because they do not scatter or reflect visible light and thus enable translucent materials.

E.g. WO 2012/64573 A1 (Shukla et al.) describes a radiopaque dental adhesive composition comprising radiopaque metal oxide nanoparticles (e.g. zirconia).

US 2003/0004294 (Moszner et al.) relates to dental materials with improved mechanical properties containing polymerizable metal oxide clusters of a particular formula. It is described that the curing of these materials can be accomplished by thermal, photochemical or redox-induced polymerization.

Incorporating zirconia nanoparticles in dental compositions, however, is not always easy as these particles are sometimes incompatible with (meth)acrylate functionalized polyalkenoic acids, especially in the presence of water. Upon mixing sometimes a kind of gellation process occurs which is not desired especially from a shelf life point of view.

DESCRIPTION OF THE INVENTION

Thus, there is a need for a dental material which is radiopaque, sufficiently storage stable and which can easily be formulated even in the presence of (meth)acrylate functionalized polyalkenoic acids.

With respect to certain embodiments, it can also be desirable, if the dental material has a colour making it useful for dental purposes.

At least one of these objects can be achieved with the dental composition as described in the present text.

Thus, in one embodiment the present invention features a curable composition for dental use comprising polyoxymetalates in an amount of at least about 5 wt.-% with respect to the weight of the composition.

The curable composition typically comprises
  a resin matrix comprising hardenable components, the hardenable components typically comprising a hardenable component with at least one acidic moiety (A1),
  an initiator system suitable for curing the hardenable components,
  polyoxometalate(s) and/or derivatives thereof being present in an amount of at least about 5 or at least about 7 or at least about 10 wt.-% with respect to the weight of the composition.

Moreover, the invention features the use of polyoxometalate and/or derivatives thereof for producing a radiopaque dental composition for dental use as described in the present text.

Definitions

Unless defined differently, for this description the following terms shall have the given meaning:

A "dental composition" or a "composition for dental use" or a "composition to be used in the dental field" is any composition which can and is to be used in the dental field. In this respect the composition should not be detrimental to the patients' health and thus free of hazardous and toxic components being able to migrate out of the composition.

Examples of dental compositions include permanent and temporary crown and bridge materials, artificial crowns, anterior or posterior filling materials and adhesives.

Dental compositions are typically hardenable compositions. Dental compositions for hardening in the mouth can be hardened at ambient conditions, including a temperature range from about 15 to 50° C. or from about 20 to 40° C. within a time frame of about 30 min or 20 min or 10 min. Higher temperatures are not recommended as they might cause pain to the patient and may be detrimental to the patient's health. Dental compositions are typically provided to the practitioner in comparatively small volumes, that is volumes in the range from about 0.1 to about 100 ml or from about 0.5 to about 50 ml or from about 1 to about 30 ml. Thus, the storage volume of useful packaging devices is typically within these ranges.

Other dental compositions for hardening outside the mouth (e.g. for the production of dentures, artificial teeth, or milling blocks) can also be hardened at elevated temperatures, including a range from about 80 to 200° C. or from about 100 to 150° C.

A "polyoxometalate cluster" or "polyoxometalate anion" (abbreviated POM anion) shall mean a discrete oxygen cluster anion generally of early transition metals, which may also include one or more of a variety of heteroatoms and that has a defined molecular structure and lacks polydispersity.

A POM anion can typically be characterized by the following formula:

$$(X_xM_mM'_nO_y)^{q-},$$

with
X being a heteroatom selected from Cu, Zn, Co, Fe, B, Ga, Rh, Al, Cr, Mn, Ni, Ti, Zr, Si, Ge P, As, Te, I, preferably from Si, P, Ge, B,
x being from about 0 to about 30 or from about 0 to about 6 or from about 0 to about 2,
m being from about 3 to about 248 or from about 5 to about 34 or from about 6 to about 12, and
n being from about 0 to about m/2, y being from about 10 to about 720 or from about 18 to about 122 or from about 24 to about 40,
with the proviso that (0≤x<m+n),
q being from about 1 to about 20 or from about 2 to about 16 or from about 3 to about 5.
M or M' being one or more early transition metal selected from for example V, Nb, Ta, Mo or W,
O being oxygen.

The metal atoms M or M' that make up the framework, called addenda atoms, are typically Mo, W, and V. If only one element M is present and x=0 and n=0, the POM is called an isopolyoxometalate. When more than one element M or M' is present and x=0, the cluster is called a mixed addenda isopolyoxometalate (n≠0).

The hetero atom, X, can be chosen from all groups on the periodic table except for, at present, the noble gases. If x≥1, the cluster is called a heterpolyoxometalate and if x≥1 and n≠0 the cluster is called a mixed addenda heteropolyoxometalate.

Isopolyoxometalates and heteropolyoxometalates are types of polyoxometalates. Polyoxometalate anions form a structurally distinct class of complexes based predominately, although not exclusively, upon quasi-octahedrally-coordinated metal atoms. The $MO_6$ units are joined together through shared edges and/or vertices, or, less commonly, faces.

Heteroatoms may be present in polyoxometalates. Different elements can act as heteroatoms, with various coordination numbers:
4-coordinate (tetrahedral) in Keggin and Dawson structures (e.g., $PO_4$, $SiO_4$);
6-coordinate (octahedral) in Anderson structure (e.g. $Al(OH)_6$, $TeO_6$);
8-coordinate (square antiprism) e.g. $((CeO_8)W_{10}O_{28})^{8-}$;

A "lacunary polyoxometalate" refers to any poloxometalate cluster anion which is deficient in one or more addenda metals creating at least one vacant site on the cluster. The vacant site allows for chemical modification of the POM, for instance, covalent tethering of organic groups through a siloxane linker. The chemical modification of a POM anion using covalent tethering of an organic group through a siloxane linker is an example of organic modification of a POM. Such complexes shall be termed "derivatives of POMs" herein. In most, but not all, cases the free lacunary polyanion is also independently stable and isolable.

Thus, the term "polyoxometalate anion" is applied to a group of discrete anionic clusters with frameworks built from transition metal polyhedra linked by shared oxo ligands. The term is generally applied to clusters of 3 or more transition metal atoms from group 5 and group 6 in their high oxidation states, (d0 and d1 configuration), e.g. V(V), Nb(V), Ta(V)), (Mo(VI) and W(VI).

A salt from a POM anion and a counter-cation is called a "POM salt". POM salts dissociate into their respective POM anions and counter cations when dissolved in a solvent, like a typical salt (e.g. NaCl in water).

A "dissolved polyoxometalate cluster" (abbreviated dissolved POM cluster) or "dissolved polyoxometalate anion" (abbreviated dissolved POM anion) shall refer to a polyoxometalate in its discrete molecular state, dissolved in (i.e., solvated by), for example, a resin matrix.

A "polyoxometalate particle" (abbreviated POM particle) shall refer to a polyoxometalate in an aggregated state (i.e., not dissolved) including counter-cations (like those described in the text below) and optionally any waters of hydration. A polyoxometalate particle may be amorphous or crystalline. POM particles can include POM salt particles, for example POM salt crystals.

Herein, the term "polyoxometalate" (abbreviated POM) shall refer to both the aggregated (i.e. POM particle) and molecular states (i.e. dissolved POM anion or dissolved POM cluster).

An "initiator system" shall include those components of the dental composition being able to start or initiate the curing process of the hardenable components, also described herein as "curing the hardenable components."

"Alpha-cleavage" shall mean the breaking of a covalent bond adjacent to a carbon bearing a specific functional group, e.g. a carbonyl group, thereby generating radicals. Typical components which can undergo alpha-cleavage and are often used in photochemistry include components comprising a carbonyl moiety, especially an aromatic carbonyl moiety, like alkylaryl ketones, benzoin derivatives, methylolbenzoin, 4-benzoyl-1,3-dioxolane derivatives, benzilketals, alpha,alpha-dialkoxyacetophenones, alpha-hydroxy alkylphenones, alpha-aminoalkylphenones, and acylphosphine oxides. Other examples can be found in: J. V. Crivello & K. Dietliker, Chemistry & Technology of UV & EB Formulation for Coatings, Inks & Paints—Volume III: Photoinitiators for Free Radical Cationic & Anionic Photopolymerization ($2^{nd}$ Edition), John Wiley & Sons, Chichester, 1998. Alpha-cleavage can be initiated by radiation (e.g. wavelength from about 200 to about 800 nm).

A "resin matrix" shall mean the organic part of the dental composition being composed of the hardenable components and organic diluents, if present.

A "hardenable component or material" (e.g., "polymerizable component" or "crosslinkable component") is any component which can be cured or solidified e.g., by heating to cause polymerization, chemical crosslinking, radiation-induced polymerization or crosslinking by using a redox initiator. A hardenable component may contain, for example, only one, two, three or more polymerizable groups. Typical examples of polymerizable groups include unsaturated carbon groups, such as a vinyl group being present e.g. in a (meth)acrylate group.

A "curable composition" is a mixture of two or more components, the mixture being able to be cured or solidified e.g., by heating to cause chemical crosslinking, radiation-induced polymerization or crosslinking by using a redox initiator. A curable composition may advantageously include a hardenable component.

A "monomer" is any chemical substance which can be characterized by a chemical formula, bearing one or more polymerizable groups (including (meth)acrylate groups) which can be polymerized to oligomers or polymers thereby increasing the molecular weight. The molecular weight of monomers can usually simply be calculated based on the chemical formula given.

As used herein, "(meth)acryl" is a shorthand term referring to "acryl" and/or "methacryl". For example, a "(meth)

acryloxy" group is a shorthand term referring to either an acryloxy group (i.e., $CH_2=CH-C(O)-O-$) and/or a methacryloxy group (i.e., $CH_2=C(CH_3)-C(O)-O-$). Similarly, (meth)acrylate is a shorthand term referring to "acrylate" and/or "methacrylate."

"Curing," "hardening," and "setting reaction" are used interchangeably and refer to a reaction wherein physical properties such as viscosity and hardness of a composition change (e.g., increase) over time due to a chemical reaction between the individual components.

An "ethylenically unsaturated acidic compound" is meant to include monomers, oligomers, and polymers having ethylenic unsaturation and acid and/or acid-precursor functionality. Acidic-precursor functionalities include, e.g. anhydrides, acid halides and pyrophosphates. The acidic group preferably comprises one or more carboxylic acid residues, such as —COOH or —CO—O—CO—, phosphoric acid residues, such as —O—P(O)(OH)OH, phosphonic acid residues such as C—P(O)(OH)OH, sulfonic acid residues, such as —$SO_3H$ or sulfinic acid residues such as —$SO_2H$.

A "powder" means a dry, bulk solid composed of a large number of very fine particles that may, for example, flow freely when shaken or tilted.

A "particle" means a substance being a solid having a shape which can be geometrically determined. Particles can typically be analysed with respect to e.g. particle size or diameter. Particles, as used herein, exhibit at least some degree of polydispersity in their size distribution, in contrast to polyoxometalate anions or clusters, which are discrete entities with defined molecular structure. Particles may be amorphous or crystalline.

"Storage stable" shall mean that the composition can be stored for at least about 1 week without exhibiting any settling (visible to the human eye) of the polyoxymetalate contained therein under ambient conditions, e.g. room temperature (about 20 to about 22° C.) and atmospheric pressure.

"Radiation curable" shall mean that the component (or composition, as the case may be) can be cured by applying radiation, preferably electromagnetic radiation with a wavelength in the visible light spectrum under ambient conditions and within a reasonable time frame (e.g. within about 15, 10 or 5 min).

The term "visible light" is used to refer to light having a wavelength of about 400 to about 700 nanometers (nm).

As used herein, "radiopaque" describes the ability of a hardened dental material to scatter X-rays from standard dental X-ray equipment, thus appearing bright on a radiograph. In contrast, radiolucent materials do not absorb or scatter X-rays and appear dark on a radiograph. In some embodiments, a radiopaque material (i.e. a material that has radiopacity) can be distinguished from radiolucent substrates like carious tooth tissue. "Hard dental tissue" means dentin and enamel.

"Ambient conditions" mean the conditions which the inventive composition is usually subjected to during storage and handling. Ambient conditions may, for example, be a pressure of about 900 to about 1100 mbar, a temperature of about −10 to about 60° C. and a relative humidity of about 10 to about 100%. In the laboratory ambient conditions can be adjusted to about 23° C. and about 1013 mbar and about 50% relative humidity. In the dental and orthodontic field ambient conditions are reasonably understood as a pressure of about 950 to about 1050 mbar, temperature of about 15 to about 40° C. and relative humidity of about 20 to about 80%.

A composition is "essentially or substantially free of" a certain component within the meaning of the invention, if the composition does not contain said component as an essential feature. Thus, said component is not willfully added to the composition either as such or in combination with other components or ingredient of other components. A composition being essentially free of a certain component usually contains the component in an amount of less than about 1 wt.-% or less than about 0.1 wt.-% or less than about 0.01 wt.-% with respect to the whole composition. Ideally, the composition or solution does not contain the said component at all. However, sometimes the presence of a small amount of the said component is not avoidable e.g. due to impurities.

As used herein, "a", "an", "the", "at least one" and "one or more" are used interchangeably. The terms "comprises" or "contains" and variations thereof do not have a limiting meaning where these terms appear in the description and claims. The term "comprising" also includes the more limited expressions "consisting essentially of" and "consisting of".

Also herein, the recitations of numerical ranges by endpoints include all numbers subsumed within that range (e.g., 1 to 5 includes 1, 1.5, 2, 2.75, 3, 3.80, 4, 5, etc.). Adding an "(s)" to a term means that the term should include the singular and plural form. E.g. the term "additive(s)" means one additive and more additives (e.g. 2, 3, 4, etc.).

Unless otherwise indicated, all numbers expressing quantities of ingredients, measurement of physical properties such as described below and so forth used in the specification and claims are to be understood as being modified in all instances by the term "about."

DETAILED DESCRIPTION OF THE INVENTION

The composition described in the present text relates to dental compositions containing polyoxometalates (POMs) and/or derivatives thereof, for example organically modified POMs, as radiopacifiers. Thus, the dental composition described in the present text is radiopaque.

Radiopacity is a desired feature especially for restorative dental materials such as filling composites, luting cements, and adhesives. Radiopacity in a dental material is advantageous in certain instances where X-rays are used to diagnose a dental condition. For example, a radiopaque material would allow the detection of secondary caries that may have formed in the tooth tissue surrounding a filling. The desired degree of radiopacity can be varied, depending upon the particular application and the expectations of the practitioner evaluating the X-ray film.

However, besides this property using POMs in a dental composition may also contribute to the other advantageous features:

POM clusters are typically soluble on a molecular level over a broad range of the formulations described herein.

Dissolved POM clusters preferably do not separate or settle over time once incorporated in the formulation and thus facilitate the production process and contribute to enhancing the shelf life of the composition. This is especially an advantage for low viscous compositions such as dental adhesives and dental sealants. Low viscous compositions typically have a viscosity in the range of 0.1 to 10,000 mPa*s; 23° C.

In addition, the small size of the dissolved POM cluster allows it to penetrate into dentin or etched enamel which has an estimated pore size of about 100 nm to about 3000 nm. On the other hand, dissolved POM clusters may also be advantageous for highly viscous compositions such as filling composites. Here, radiopacity is typically imparted by the inorganic filler present in the compositions. Dissolving POM clusters in the resin matrix may further enhance radiopacity, without increasing the filler load over an undesirable level, which could, for instance, impart difficult handling of the composition.

Using dissolved POM clusters may also contribute to providing highly translucent materials. Without wishing to be bound to a certain theory, it is believed that this is caused by the small molecular size the POM(s) typically have and the ability to form real solutions and not only dispersions (i.e, dispersions of particles) within the resin matrix. If the size of a component is less than the wave length of visible light, the light scattering and reflectance is reduced and the material becomes more translucent.

Further, POMs are typically compatible with other components contained in dental materials, such as polyalkenoic acids, even in the presence of water. It has been observed that compositions containing nano-zirconia materials sometimes tend to form gels especially if the composition comprises polyalkenoic acids.

It was found that this tendency can be reduced or even prevented, if the nano-zirconia material is avoided in the composition, and if POM(s) are used as a radiopaque additive. Thus, it has been discovered that polyoxometalate clusters can be homogeneously dissolved in dental formulations and enable the practitioner to provide radiopaque, storage stable and translucent materials. In some embodiments, it may be advantageous to use POM particle(s).

In highly viscous systems, in which the POM cluster(s) are not soluble, the POM particle(s) may provide the desired radiopacity without separating from the composition. It was also found that the POM components described in the present text are compatible with components comprising an acidic moiety. Thus, the present invention enables the formulation of storage stable, radiopaque acidic compositions. Further, depending on the initiator system, the obtained composition does not show undesired colouring, which may be caused by an unwanted reaction between the POM clusters or particles with initiators components.

The composition described in the present text is radiation curable and thus comprises hardenable components which can be cured by applying radiation. The hardenable components are parts to the resin matrix of the composition. The resin matrix may comprise hardenable components with one or more acidic moieties as component (A1), hardenable components without acidic moieties as component (A2) or combinations of hardenable components with acidic moieties and curable components without acidic moieties.

The resin matrix is typically contained in the following amounts. The amount is given with respect to the weight of the whole composition.

Lower limit: at least about 5 or at least about 10 or at least about 20;
Upper limit: utmost about 95 or utmost about 80 or utmost about 70;
Range: from about 5 to about 95 or from about 10 to about 80.

According to one embodiment, the composition described in the present text comprises a hardenable component with at least one acidic moiety. If desired, a mixture of different radiation curable components, each with one or more acidic moieties, can be used.

By adding a hardenable component with at least one acidic moiety to the composition, the composition will become acidic and able to etch the surface of hard dental tissue. This property typically contributes to make the composition self-etching and also self-adhesive. Certain hardenable components with one or more acidic moieties (A1) are sometimes also referred to as ethylenically unsaturated components with acidic moiety and can be characterized by at least one or all of the following features:

Molecular weight (Mw): from about 70 to about 700 g/mol or from about 100 to about 600 or from about 200 to about 500 g/mol, Viscosity: from about 0.1 to about 10 Pa*s, or from about 0.2 to about 5 Pa*s or from about 0.5 to about 2 Pa*s measured at 23° C., and/or Refractive index: from about 1.42 to about 1.55 (nD).

The hardenable components with acid moiety (A1) can typically be represented by the following formula

$A_n\text{-}B\text{—}C_m$ with A being an ethylenically unsaturated group, such as a (meth)acryl moiety, B being a spacer group, such as (i) linear or branched C1 to C12 alkyl, optionally substituted with other functional groups (e.g. halogenides (including Cl, Br, I), OH or mixtures thereof) (ii) C6 to C12 aryl, optionally substituted with other functional groups (e.g. halogenides, OH or mixtures thereof), (iii) organic group having 4 to 20 carbon atoms bonded to one another by one or more ether, thioether, ester, thioester, thiocarbonyl, amide, urethane, carbonyl and/or sulfonyl linkages, and C being an acidic group, m, n being independently selected from 1, 2, 3, 4, 5 or 6, wherein the acidic group comprises one or more carboxylic acid residues, such as —COOH or —CO—O—CO—, phosphoric acid residues, such as —O—P(O)(OH)OH, phosphonic acid residues, such as C—P(O)(OH)(OH), sulphonic acid residues, such as —SO$_3$H or sulfinic acid residues such as —SO$_2$H.

Examples of hardenable components with acid moiety include, but are not limited to glycerol phosphate mono (meth)acrylate, glycerol phosphate di(meth)acrylate, hydroxyethyl (meth)acrylate (e.g., HEMA) phosphate, bis((meth)acryloxyethyl) phosphate, (meth)acryloxypropyl phosphate, bis((meth)acryloxypropyl) phosphate, bis((meth)acryloxy)propyloxy phosphate, (meth)acryloxyhexyl phosphate, bis((meth)acryloxyhexyl) phosphate, (meth)acryloxyoctyl phosphate, bis((meth)acryloxyoctyl) phosphate, (meth)acryloxydecyl phosphate, bis((meth)acryloxydecyl) phosphate, caprolactone methacrylate phosphate, citric acid di- or tri-methacrylate, poly(meth)acrylated oligomaleic acid, poly(meth)acrylated polymaleic acid, poly(meth)acrylated poly(meth)acrylic acid, poly(meth)acrylated polycarboxyl-polyphosphonic acid, poly(meth)acrylated polychlorophosphoric acid, poly(meth)acrylated polysulfonate, poly(meth)acrylated polyboric acid, and the like. Derivatives of these hardenable components bearing an acid moiety that can readily react e.g. with water to form the specific examples mentioned above, like acid halides or anhydrides are also contemplated.

Also monomers, oligomers, and polymers of unsaturated carboxylic acids such as (meth)acrylic acids, aromatic (meth)acrylated acids (e.g., methacrylated trimellitic acids), and anhydrides thereof can be used.

Some of these compounds can be obtained, e.g., as reaction products between isocyanatoalkyl (meth)acrylates and carboxylic acids. Additional compounds of this type having both acid-functional and ethylenically unsaturated components are described in U.S. Pat. No. 4,872,936 (Engelbrecht) and U.S. Pat. No. 5,130,347 (Mitra). A wide variety of such compounds containing both the ethylenically unsaturated and acid moieties can be used. If desired, mixtures of such compounds can be used.

Using (meth)acrylate functionalized polyalkenoic acids is often preferred as those components were found to be useful to improve properties like adhesion to hard dental tissue, formation of a homogeneous layer, viscosity, or moisture tolerance. According to one embodiment, the composition contains (meth)acrylate functionalized polyalkenoic acids, for example, AA:ITA:IEM (copolymer of acrylic acid:itaconic acid with pendent methacrylates).

These components can be made by reacting e.g. an AA:ITA copolymer with 2-isocyanatoethyl methacrylate to convert at least a portion of the acid groups of the copolymer to pendent methacrylate groups. Processes for the production of these components are described, e.g., in Example 11 of U.S. Pat. No. 5,130,347 (Mitra); and those recited in U.S. Pat. No. 4,259,075 (Yamauchi et al.), U.S. Pat. No. 4,499,251 (Omura et al.), U.S. Pat. No. 4,537,940 (Omura et al.), U.S. Pat. No. 4,539,382 (Omura et al.), U.S. Pat. No. 5,530,038 (Yamamoto et al.), U.S. Pat. No. 6,458,868 (Okada et al.), and EP 0 712 622 A1 (Tokuyama Corp.) and EP 1 051 961 A1 (Kuraray Co., Ltd.).

The unsaturated acidic compound (A1) can be present in the composition in an amount of at least about 3 or at least about 5 or at least about 10 wt.-%, wt.-% with respect to the weight of the whole composition. However, amounts of up to about 80 or up to about 70 or up to about 60 wt.-% can still be useful, wt.-% with respect to the weight of the whole composition. Useful amounts include from about 3 to about 80 or from about 5 to about 70 or from about 10 to about 60 wt.-% with respect to the weight of the whole composition.

The resin matrix may also comprise one or more hardenable component(s) without an acid moiety as component (A2). This component is typically a free-radically polymerizable material, including ethylenically unsaturated monomer, monomers or oligomers or polymers. Suitable hardenable components without an acidic moiety can be characterized by the following formula:

$A_n\text{-}B\text{-}A_m$ with A being an ethylenically unsaturated group, such as a (meth)acryl moiety, B being selected from (i) linear or branched C1 to C12 alkyl, optionally substituted with other functional groups (e.g. halogenides (including Cl, Br, I), OH or mixtures thereof) (ii) C6 to C12 aryl, optionally substituted with other functional groups (e.g. halogenides, OH or mixtures thereof), or (iii) organic group having 4 to 20 carbon atoms bonded to one another by one or more ether, thioether, ester, thioester, thiocarbonyl, amide, urethane, carbonyl and/or sulfonyl linkages, m, n being independently selected from 0, 1, 2, 3, 4, 5 or 6 with the proviso that n+m is greater 0, that is that at least one A group is present.

Such polymerizable materials include mono-, di- or polyacrylates and methacrylates such as methyl acrylate, methyl methacrylate, ethyl (meth)acrylate, isopropyl (meth)acrylate, n-hexyl (meth)acrylate, stearyl (meth)acrylate, allyl (meth)acrylate, glycerol di(meth)acrylate, the diurethane dimethacrylate called UDMA (mixture of isomers, e.g. Röhm Plex 6661-0) being the reaction product of 2-hydroxyethyl methacrylate (HEMA) and 2,2,4-trimethylhexamethylene diisocyanate (TMDI), glycerol tri(meth)acrylate, ethyleneglycol di(meth)acrylate, diethyleneglycol di(meth)acrylate, triethyleneglycol di(meth)acrylate, 1,3-propanediol diacrylate, 1,3-propanediol dimethacrylate, trimethylolpropane tri(meth)acrylate, 1,2,4-butanetriol tri(meth)acrylate, 1,4-cyclohexanediol di(meth)acrylate, pentaerythritol tri(meth)acrylate, pentaerythritol tetraacrylate, pentaerythritol tetramethacrylate, sorbitol hexa(meth)acrylate, bis[1-(2-(meth)acryloxy)]-p-ethoxyphenyldimethylmethane, bis[1-(3-methacryloxy-2-hydroxy)]-p-propoxyphenyldimethylmethane (BisGMA), bis[1-(3-acryloxy-2-hydroxy)]-p-propoxy-phenyldimethylmethane and trishydroxyethyl-isocyanurate trimethacrylate; the bis-acrylates and bis-methacrylates of polyethylene glycols of molecular weight 200-500, copolymerizable mixtures of acrylated monomers (see e.g. U.S. Pat. No. 4,652,274), and acrylated oligomers (see e.g. U.S. Pat. No. 4,642,126); and vinyl compounds such as styrene, diallyl phthalate, divinyl succinate, divinyl adipate and divinylphthalate; polyfunctional (meth)acrylates comprising urethane, urea or amide groups. Mixtures of two or more of these free radically polymerizable materials can be used if desired.

These ethylenically unsaturated monomers can be employed in the dental composition(s) either alone or in combination with other ethylenically unsaturated monomers. Monomers comprising a hydroxyl moiety can also be added. Suitable compounds include 2-hydroxyethyl (meth) acrylate (HEMA), 2- or 3-hydroxypropyl (meth)acrylate, 4-hydroxybutyl (meth)acrylate, 5-hydroxypentyl (meth) acrylate, 6-hydroxyhexyl (meth)acrylate, 10-hydroxydecyl (meth)acrylate, dialkylene glycol mono(meth)acrylate, for example, diethylene glycol mono(meth)acrylate, triethylene glycol mono(meth)acrylate, tetraethylene glycol mono (meth)acrylate, polyethylene glycol mono(meth)acrylate, dipropylene glycol mono(meth)acrylate, polypropylene glycol mono(meth)acrylate, and further 1,2- or 1,3- and 2,3-dihydroxypropyl (meth)acrylate, 2-hydroxypropyl-1,3-di (meth)acrylate, 3-hydroxypropyl-1,2-di(meth)acrylate, N-(meth)acryloyl-1,2-dihydroxypropylamine, N-(meth) acryloyl-1,3-dihydroxypropylamine, adducts of phenol and glycidyl (meth)acrylate, for example, 1-phenoxy-2-hydroxypropyl (meth)acrylate, 1-naphthoxy-2-hydroxypropyl (meth)acrylate, bisphenol A diglycidyl (meth)acrylate and the like, 2-hydroxyethyl (meth)acrylate, 2-hydroxypropyl (meth)acrylate and 2,3-dihydroxypropyl (meth)acrylate are particularly preferable. If desired, mixtures of one or more of these components can be used.

In addition or besides those components, other hardenable components which can be added include oligomeric or polymeric compounds, such as polyester urethane (meth) acrylates, polyether urethane (meth)acrylates, polycarbonate urethane (meth)acrylates and poly(meth)acrylate urethane (meth)acrylates. The molecular weight of these compounds is typically less than 20,000 g/mol, particularly less than 15,000 g/mol and in particular less than 10,000 g/mol.

Adding these components may be used to adjust the rheological properties. If present, the amount of component (A2) contained in the composition is typically up to about 65 wt.-% or up to about 55 wt.-% or up to about 45 wt.-% with respect to the weight of the whole composition. Typical ranges for component (A2) may include from about 5 to about 65 or from about 10 to about 55 or from about 20 to about 45 or wt.-% with respect to the weight of the whole composition.

The initiator system can comprise systems which are capable of initiating polymerization via radiation, heat, e-beam or redox/auto-cure, chemical reaction. A radiation curable dental composition typically contains a radiation sensitive initiator system as component (B).

The nature of the initiator system is not particularly limited as long as the initiator system is suitable to initiate the curing of the curable components contained in the resin matrix in which the POM is dissolved. However, the initiator system used for curing the dental composition described in the present text is not POM based. A class of initiators capable of initiating polymerization of the hardenable components of the resin matrix which contain free radically active functional groups includes free radical-generating photoinitiators, optionally combined with a photosensitizer or accelerator. Such initiators typically can be capable of generating free radicals for addition polymerization upon exposure to light energy having a wavelength between about 200 and about 700 nm. Initiator components which can undergo an alpha-cleavage are sometimes preferred.

Using acylphosphine oxides as initiators or part of the initiator system was found to be particularly useful. Suitable acylphosphine oxides can be characterized by the following formula:

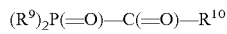

wherein each $R^9$ individually can be a hydrocarbyl group such as alkyl, cycloalkyl, aryl, and aralkyl, any of which can be substituted with a halo-, alkyl- or alkoxy-group, or the two $R^9$ groups can be joined to form a ring along with the phosphorous atom, and wherein $R^{10}$ is a hydrocarbyl group, an S-, O-, or N-containing five- or six-membered heterocyclic group, or a —Z—C(=O)—P(=O)—$(R^9)_2$ group, wherein Z represents a divalent hydrocarbyl group such as alkylene or phenylene having from 2 to 6 carbon atoms. Suitable systems are also described e.g. in U.S. Pat. No. 4,737,593, the content of which is herewith incorporated by reference.

Preferred acylphosphine oxides useful in the invention are those in which the $R^9$ and $R^{10}$ groups are phenyl or lower alkyl- or lower alkoxy-substituted phenyl. By "lower alkyl" and "lower alkoxy" is meant such groups having from 1 to 4 carbon atoms. Most preferably, the acylphosphine oxide is 2,4,6-trimethylbenzoyl diphenyl phosphine oxide (Lucirin™ TPO, BASF).

Suitable bisacylphosphine oxides can also be described by the following formula:

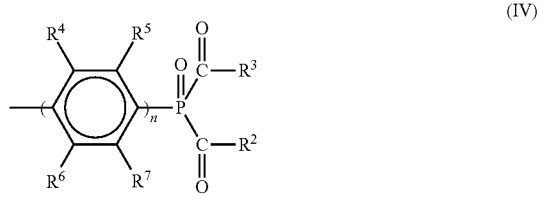

(IV)

wherein n is 1 or 2, and $R^4$, $R^5$, $R^6$ and $R^7$ are H, C1-4 alkyl, C1-4 alkoxyl, F, Cl or Br; $R^2$ and $R^3$, which are the same or different, stand for a cyclohexyl, cyclopentyl, phenyl, naphthyl, or biphenylyl radical, a cyclopentyl, cyclohexyl, phenyl, naphthyl, or biphenylyl radical substituted by F, Cl, Br, I, C1-4 alkyl and/or C1-4 alkoxyl, or an S or N-containing 5-membered or 6-membered heterocyclic ring; or $R^2$ and $R^3$ are joined to form a ring containing from 4 to 10 carbon atoms and being optionally substituted by 1 to 6 C1-4 alkyl radicals.

More specific examples include: bis-(2,6-dichlorobenzoyl)phenylphosphine oxide, bis-(2,6-dichlorobenzoyl)-2,5-dimethylphenylphosphine oxide, bis-(2,6-dichlorobenzoyl)-4-ethoxyphenylphosphine oxide, bis-(2,6-dichlorobenzoyl)-4-biphenylylphosphine oxide, bis-(2,6-dichlorobenzoyl)-4-propylphenylphosphine oxide, bis-(2,6-dichlorobenzoyl)-2-naphthylphosphine oxide, bis-(2,6-dichlorobenzoyl)-1-napthylphosphine oxide, bis-(2,6-dichlorobenzoyl)-4-chlorophenylphosphine oxide, bis-(2,6-dichlorobenzoyl)-2,4-dimethoxyphenylphosphine oxide, bis-(2,6-dichlorobenzoyl)decylphosphine oxide, bis-(2,6-dichlorobenzoyl)-4-octylphenylphosphine oxide, bis-(2,6-dimethoxybenzoyl)-2,5-dimethylphenylphosphine oxide, bis-(2,6-dimethoxybenzoyl)phenylphosphine oxide, bis-(2,4,6-trimethylbenzoyl)-2,5-dimethylphenylphosphine oxide, bis-(2,6-dichloro-3,4,5-trimethoxybenzoyl)-2,5-dimethylphenylphosphine oxide, bis-(2,6-dichloro-3,4,5-trimethoxybenzoyl)-4-ethoxyphenylphosphine oxide, bis-(2-methyl-1-naphthoyl)-2,5-dimethylphenylphosphine oxide, bis-(2-methyl-1-naphthoyl)phenylphosphine oxide. bis-(2-methyl-1-naphthoyl)-4-biphenylylphosphine oxide, bis-(2-methyl-1-naphthoyl)-4-ethoxyphenylphosphine oxide, bis-(2-methyl-1-naphthoyl)-2-naphthylphosphine oxide, bis-(2-methyl-1-naphthoyl)-4-propylphenylphosphine oxide, bis-(2-methyl-1-naphthoyl)-2,5-dimethylphosphine oxide, bis-(2-methoxy-1-naphthoyl)-4-ethoxyphenylphosphine oxide, bis-(2-methoxy-1-naphthoyl)-4-biphenylylphosphine oxide, bis-(2-methoxy-1-naphthoyl)-2-naphthylphosphine oxide and bis-(2-chloro-1-naphthoyl)-2,5-dimethylphenylphosphine oxide.

The acylphosphine oxide bis(2,4,6-trimethylbenzoyl)phenyl phosphine oxide (IRGACURE™ 819, Ciba Specialty Chemicals, Tarrytown, N.Y.) is sometimes preferred. Tertiary amine reducing agents may be used in combination with an acylphosphine oxide. Illustrative tertiary amines useful in the invention include ethyl 4-(N,N-dimethylamino)benzoate (EDMAB) and N,N-dimethylaminoethyl methacrylate (DMAEMA). Commercially-available phosphine oxide photoinitiators capable of free-radical initiation when irradiated at wavelengths of greater than 400 nm to 1200 nm include a 25:75 mixture, by weight, of bis(2,6-dimethoxybenzoyl)-2,4,4-trimethylpentyl phosphine oxide and 2-hydroxy-2-methyl-1-phenylpropan-1-one (IRGACURE™ 1700, Ciba Specialty Chemicals), 2-benzyl-2-(N,N-dimethylamino)-1-(4-morpholinophenyl)-1-butanone (IRGACURE™ 369, Ciba Specialty Chemicals), bis(η5-2,4-cyclopentadien-1-yl)-bis(2,6-difluoro-3-(1H-pyrrol-1-yl)phenyl) titanium (IRGACURE™ 784 DC, Ciba Specialty Chemicals), a 1:1 mixture, by weight, of bis(2,4,6-trimethylbenzoyl)phenyl phosphine oxide and 2-hydroxy-2-methyl-1-phenylpropane-1-one (DAROCUR™ 4265, Ciba Specialty Chemicals), and ethyl-2,4,6-trimethylbenzylphenyl phosphinate (LUCIRIN™ LR8893X, BASF Corp., Charlotte, N.C.).

A variety of visible or near-IR photoinitiator systems may also be used for photopolymerization of free-radically polymerizable materials. For example, a photoinitiation system can be used selected from systems which initiate polymerization via a two component system of an amine and an α-diketone. Such systems are described e.g. in U.S. Pat. No. 4,071,424 and WO 2009151957, which are herein incorporated by reference.

Alternatively, the resin can be combined with a three components or ternary photoinitiator system. Suitable systems are described in U.S. Pat. No. 5,545,676 and WO 2009151957, which are incorporated herein by reference. In the ternary photoinitiator system, the first component is an iodonium salt, i.e., a diaryliodonium salt. The iodonium salt is preferably soluble in the monomer and shelf-stable (ie., does not spontaneously promote polymerization) when dissolved therein in the presence of the sensitizer and donor. Accordingly, selection of a particular iodonium salt may depend to some extent upon the particular monomer, polymer or oligomer, sensitizer and donor chosen. Suitable iodonium salts are described in U.S. Pat. No. 3,729,313, U.S. Pat. No. 3,741,769, U.S. Pat. No. 3,808,006, U.S. Pat. No. 4,250,053 and U.S. Pat. No. 4,394,403, the iodonium salt disclosures of which are incorporated herein by reference. The iodonium salt can be a simple salt (e.g., containing an anion such as $Cl^-$, $Br^-$, $I^-$ or $C_4H_5SO_3^-$) or a metal complex salt (e.g., containing $SbF_5OH^-$ or $AsF_6^-$). Mixtures of iodonium salts can be used if desired. Preferred iodonium salts include diphenyliodonium salts such as diphenyliodonium chloride, diphenyliodonium hexafluorophosphate and diphenyliodonium tetrafluoroborate.

The second component in a ternary photoinitiator system is a sensitizer. The sensitizer desirably is soluble in the monomer, and is capable of light absorption somewhere within the range of wavelengths of greater than 400 to 1200 nanometers, more preferably greater than 400 to 700 nanometers and most preferably greater than 400 to about 600 nanometers. The sensitizer may also be capable of sensitizing 2-methyl-4,6-bis(trichloromethyl)-s-triazine, using the test procedure described in U.S. Pat. No. 3,729,313, which is incorporated herein by reference. Preferably, in addition to passing this test, a sensitizer is also selected based in part upon shelf stability considerations. Accordingly, selection of a particular sensitizer may depend to some extent upon the particular monomer, oligomer or polymer, iodonium salt and donor chosen.

Suitable sensitizers can include compounds in the following categories: ketones, coumarin dyes (e.g., ketocoumarins), xanthene dyes, acridine dyes, thiazole dyes, thiazine dyes, oxazine dyes, azine dyes, aminoketone dyes, porphyrins, aromatic polycyclic hydrocarbons, p-substituted aminostyryl ketone compounds, aminotriaryl methanes, merocyanines, squarylium dyes and pyridinium dyes. Ketones (e.g., monoketones or alpha-diketones), ketocoumarins, aminoarylketones and p-substituted aminostyryl ketone compounds are preferred sensitizers. For applications requiring high sensitivity, it is preferred to employ a sensitizer containing a julolidinyl moiety. For applications requiring deep cure (e.g., cure of highly-filled composites), it is preferred to employ sensitizers having an extinction coefficient below about 1000, more preferably below about 100, at the desired wavelength of irradiation for photopolymerization. Alternatively, dyes that exhibit reduction in light absorption at the excitation wavelength upon irradiation can be used.

For example, a preferred class of ketone sensitizers has the formula: $ACO(X)_b B$, where X is CO or $CR^5 R^6$, where $R^5$ and $R^6$ can be the same or different, and can be hydrogen, alkyl, alkaryl or aralkyl, b is zero or one, and A and B can be the same or different substituted (having one or more non-interfering substituents) or unsubstituted aryl, alkyl, alkaryl, or aralkyl groups, or together A and B can form a cyclic structure which can be a substituted or unsubstituted cycloaliphatic, aromatic, heteroaromatic or fused aromatic ring.

Suitable ketones of the above formula include monoketones (b=0) such as 2,2-, 4,4- or 2,4-dihydroxybenzophenone, di-2-pyridyl ketone, di-2-furanyl ketone, di-2-thiophenyl ketone, benzoin, fluorenone, chalcone, Michler's ketone, 2-fluoro-9-fluorenone, 2-chlorothioxanthone, acetophenone, benzophenone, 1- or 2-acetonaphthone, 9-acetylanthracene, 2-, 3- or 9-acetylphenanthrene, 4-acetylbiphenyl, propiophenone, n-butyrophenone, valerophenone, 2-, 3- or 4-acetylpyridine, 3-acetylcoumarin and the like. Suitable diketones include aralkyldiketones such as anthraquinone, phenanthrenequinone, o-, m- and p-diacetylbenzene, 1,3-, 1,4-, 1,5-, 1,6-, 1,7- and 1,8-diacetylnaphthalene, 1,5-, 1,8- and 9,10-diacetylanthracene, and the like. Suitable alpha-diketones (b=1 and X=CO) include 2,3-butanedione, 2,3-pentanedione, 2,3-hexanedione, 3,4-hexanedione, 2,3-heptanedione, 3,4-heptanedione, 2,3-octanedione, 4,5-octanedione, benzil, 2,2'-3 3'- and 4,4'-dihydroxylbenzil, furil, di-3,3'-indolylethanedione, 2,3-bornanedione (camphorquinone), biacetyl, 1,2-cyclohexanedione, 1,2-naphthaquinone, acenaphthaquinone, and the like.

The third component of a ternary initiator system is a donor. Preferred donors include, for example, amines (including aminoaldehydes and aminosilanes), amides (including phosphoramides), ethers (including thioethers), ureas (including thioureas), ferrocene, sulfinic acids and their salts, salts of ferrocyanide, ascorbic acid and its salts, dithiocarbamic acid and its salts, salts of xanthates, salts of ethylene diamine tetraacetic acid and salts of tetraphenylboronic acid. The donor can be unsubstituted or substituted with one or more non-interfering substituents. Particularly preferred donors contain an electron donor atom such as a nitrogen, oxygen, phosphorus, or sulfur atom, and an abstractable hydrogen atom bonded to a carbon or silicon atom alpha to the electron donor atom. A wide variety of donors is disclosed in U.S. Pat. No. 5,545,676, which is incorporated herein by reference.

Another free-radical initiator system that can alternatively be used in the dental compositions described in the present text is the class of ionic dye counterion complex initiators comprising a borate anion and a complementary cationic dye. Borate salt photoinitiators are described, for example, in U.S. Pat. No. 4,772,530, U.S. Pat. No. 4,954,414, U.S. Pat. No. 4,874,450, U.S. Pat. No. 5,055,372, and U.S. Pat. No. 5,057,393, the disclosures of which are incorporated herein by reference.

Borate anions useful in these photoinitiators generally can be of the formula $R^1R^2R^3R^4B^-$, wherein $R^1$, $R^2$, $R^3$, and $R^4$ independently can be alkyl, aryl, alkaryl, allyl, aralkyl, alkenyl, alkynyl, alicyclic and saturated or unsaturated heterocyclic groups. Preferably, $R^2$, $R^3$, and $R^4$ are aryl groups and more preferably phenyl groups, and $R^1$ is an alkyl group and more preferably a secondary alkyl group.

Cationic counterions can be cationic dyes, quaternary ammonium groups, transition metal coordination complexes, and the like. Cationic dyes useful as counterions can be cationic methine, polymethine, triarylmethine, indoline, thiazine, xanthene, oxazine or acridine dyes. More specifically, the dyes may be cationic cyanine, carbocyanine, hemicyanine, rhodamine, and azomethine dyes. Specific examples of useful cationic dyes include Methylene Blue, Safranine O, and Malachite Green. Quaternary ammonium groups useful as counterions can be trimethylcetylammonium, cetylpyridinium, and tetramethylammonium. Other organophilic cations can include pyridinium, phosphonium, and sulfonium.

Photosensitive transition metal coordination complexes that may be used include complexes of cobalt, ruthenium, osmium, zinc, iron, and iridium with ligands such as pyridine, 2,2'-bipyridine, 4,4'-dimethyl-2,2'-bipyridine, 1,10-phenanthroline, 3,4,7,8-tetramethylphenanthroline, 2,4,6-tri (2-pyridyl-s-triazine) and related ligands.

In another alternative class of initiators capable of initiating polymerization of free radically active functional groups includes conventional chemical initiator systems such as a combination of a peroxide and an amine. These initiators, which rely upon a thermal redox reaction, are often referred to as "auto-cure catalysts". They are typically supplied as two-part systems in which the reactants are stored apart from each other and then combined immediately prior to use.

In a further alternative, heat may be used to initiate the hardening, or polymerization, of free radically active groups. Examples of heat sources suitable for the dental materials described in the present text include inductive, convective, and radiant. Thermal sources should be capable of generating temperatures of at least 40° C. to 15° C. This procedure is sometime preferred for initiating polymerization of materials occurring outside of the oral environment.

Yet another alternative class of initiators capable of initiating polymerization of free radically active functional groups that are useful for the dental materials as described in the present text are those that include free radical-generating thermal initiators. Examples include peroxides such as, for example, benzoyl peroxide and lauryl peroxide, and azo compounds such as, for example, 2,2-azobis-isobutyronitrile (AIBN).

If the color of the cured composition matters, an initiator system which does not lead to undesired discoloration should be used. It was found that an initiator system comprising the following components is particularly useful: monoacylphosphine oxides and/or bisacylphosphine oxides. According to one embodiment, the initiator system comprises monoacylphosphine oxide(s) and/or bisacylphosphine oxide(s) in combination with a reducing agent being selected from tertiary amines not containing an aromatic substituent attached to the N-atom of the amine moiety.

Preferred tertiary amines include N,N-dimethylaminoethyl (meth)acrylate, 3-dimethylaminopropyl (meth)acrylate, 4-dimethylaminobutyl (meth)acrylate, 6-dimethylaminohexyl (meth)acrylate, 10-dimethylaminodecyl (meth) acrylate, triethanolamine, methyl diethanolamine, 2-dimethylamino ethanol, triethylamine, tripropylamine, tributylamine, tetramethyl ethylenediamine, and combinations thereof. It was found that this combination is particularly useful if, discoloration should be avoided.

Without wishing to be bound to a particular theory, it is assumed that tertiary amines containing an aromatic substituent attached to the N-atom of the amine moiety may cause discoloration by a proton-coupled electron transfer between the aromatic moiety and POM during irradiation. According to a further embodiment, the initiator system does not contain a 1,2 diketone component, like camphorchinone.

It was found that the presence of a 1,2 diketone component, especially in combination with an amine with an aromatic moiety attached to the amine function, may lead to an undesired colouring of the composition during and after curing.

The initiator system is typically present in the following amounts. The amount is given with respect to the weight of the whole composition.
  Lower limit: at least about 0.1 or at least about 0.2 or at least about 0.3 wt.-%;
  Upper limit: utmost about 5 or utmost about 3 or utmost about 1 wt.-%;
  Range: from about 0.1 to about 5 or from about 0.2 to about 3 wt.-% or from about 0.3 to about 1 wt.-%.

The dental composition described in the present text contains a POM and/or derivative thereof or a mixture of two, three or more POMs as component C. POM may be used in the form of dissolved POM cluster(s), POM particles or combinations thereof. In one embodiment, POM is used in the form of dissolved POM cluster(s).

In most embodiments, the POM cluster(s) are soluble in the resin matrix on a molecular level (i.e., POM is present as dissolved POM clusters). That is, POM and the hardenable components of the resin matrix typically form a real solution and not only a nanoparticle-dispersion as nanofillers normally do. POM cluster(s) described in the present text are typically soluble in the resin matrix (giving dissolved POM clusters in the resin matrix; i.e., a composition that includes a resin matrix and dissolved POM clusters has POM clusters dissolved in the resin matrix).

The POM clusters described in the present text may be charge-balanced (sometimes referred to as neutralized) by counterions (also referred to herein as counter-cations). POM salts provide an example of a type of POM-based component having both the POM clusters (anions) and counter-cations present in proportions necessary to preserve electroneutrality, as is understood in the art of salt components.

Dissolved POM clusters (anions) may be charge-balanced by counter-cations that are dissociated from the POM clusters, as is understood in the art of salt solutions. Counter-cations, present in association or aggregated state with the POM cluster (e.g., in salt or acid form) or dissociated from the POM cluster in dissolved form, may be in the form of, for example, monovalent, divalent, trivalent, or tetravalent cations. Alternatively, the counter-cations may be in the form of cationic polymer.

According to some embodiments, the POM cluster(s) described in the present text are charge-balanced (sometimes referred to as neutralized) by counter-cations, wherein the POM anions(s) can be characterized by the following formula: $(X_xM_mM'_nO_y)^{q-}$,
with
X being a heteroatom selected from Si, P, Ge, B or As,
M or M' being selected from V, Nb, Ta, Mo or W, with W, Mo and V being sometimes preferred,
O being oxygen,
x being from about 0 to about 30 or from about 0 to about 6 or from about 0 to about 2,
m being from about 3 to about 248 or from about 5 to about 34 or from about 6 to about 12 and
n being from about 0 to about m/2, y being from about 10 to about 720 or from about 18 to about 122 or from about 24 to about 40,
with the proviso that $0 \le x < m+n$,
q being from about 1 to about 20 or from about 2 to about 16 or from about 3 to about 5.

The counter ion (also referred to herein as the counter-cation) can be selected from, for example, alkaline metals (e.g. Li, Na, K, Rb, Cs) or organo ammonium compounds or cationic polymers Examples of organo ammonium compounds include $NR_4^+$, with R being selected from H, C1 to C16 alkyl or C1 to C12 aryl optionally comprising in addition one or more unsaturated moieties like (meth)acryl or vinyl.

A cationic polymer comprises cationic repeating units comprising positively charged elements like N, S or P (i.e. ammonium, sulfonium and/or phosphonium moieties). The cationic polymer may also include polymerizable moieties like carbon-carbon unsaturated groups including (meth) acryl, vinyl, styryl or allyl. The molecular mass of the cationic polymer may be in the range of about 500 to about 500,000 or from about 1000 to about 250,000 or from about 10,000 to about 100,000.

Examples of suitable cationic polymers include poly [(methacryloyloxethyl)trimethylammonium chloride], poly [(methacryloylamino)propyl)trimethylammonium chloride], poly[(acrylamid-opropyl)trimethylammonium chloride], poly[(acryloyloxyethyl)trimethylammonium chloride], polyallylamine hydrochloride, polydiallyldimethylammonium chloride and mixtures thereof.

Using POM cluster(s) with Li as counter cation (i.e., charge balanced by Li cations) can be preferred. It was found that Li compounds of POM(s) often have better compatibility and/or solubility in the components of the resin matrix, enabling the preparation of compositions having dissolved POM clusters with greater ease or with higher dissolved POM concentration.

It was found that the charge of the POM cluster can have an influence on the stability, in particular storage stability, of the POM component. E.g. certain POM clusters may ionically cross-link in an acidic environment, which may lead to precipitation of the component and thus an unstable formulation. Using POM(s) having a charge in the range of −2 to −10 or −2 to −8 or −2 to −6 may help to minimize this risk. According to another embodiment, POM is used in the form of POM particles.

POM particles can be obtained from dissolved POM clusters by drying (e.g. evaporation, spray drying, lyophilization) of a POM containing solution, followed by grinding or dispersing the solid residue, or by precipitation or crystallization from a POM containing solution and collection of the resulting solid by filtration.

One example of a POM particle is a POM salt (crystalline or amorphous) particle, which can be obtained as described above. The selection of counterion can determine the ultimate solubility of a POM salt in a give resin matrix. For example, less soluble POM salts can, for some matrix resin compositions, include the following counter-cations: tetrabutylammonium, caesium, trimethylsulfonium, pyridinium, diisopropylammonium, guanadinium and imidazolium.

The dental composition described in the present text may not only comprise one type of POM. The dental composition may comprise at least one, two, three, four, five, six or more POMs of different chemical formula. The POM component(s) can also comprise organic groups or moieties like branched or straight alkyl (e.g. C1 to C12 or in some embodiments C2 to C6), in particular butyl, substituted or unsubstituted aryl, in particular phenyl or groups comprising a polymerizable moiety, in particular (meth)acryloyloxypropyl or vinyl.

The organic group may be attached directly to the POM through chemical modification of the metal oxide framework (e.g., as described above for lacunary POMs) or it may be incorporated in the form of an organic counter-cation to the POM anion. POM component(s) comprising an organic group containing a polymerizable moiety can be preferred, as these kinds of components are not only highly soluble but can also be co-polymerized with the other hardenable components contained in the resin matrix. This may further enhance the stability of POM in the resin matrix.

In some embodiments, such an organic group containing a polymerizable moiety can be covalently tethered to a POM cluster (i.e., attached directly to the POM through chemical modification of the metal oxide framework) or POM particle. In other embodiments, such an organic group containing a polymerizable moiety can be an organic counter-cation to a POM anion. POM(s) comprising e.g. organic moieties are also referred to as derivatives of POM(s). POM(s) can be produced according to processes described in the prior art and known to the skilled person. Examples, how to produce POM(s), are given in the Example section below.

In contrast to a surface-treatment of filler particles, some modifications of the POM(s) described in the present text are the covalent attachment or tethering of the functional groups; i.e. the organic moiety is implemented into the structure of the POM component.

On the other hand, organic functionalities can be incorporated through electrostatic interactions with the POM(s) by ion-exchange or salt metathesis with, for example, desired organoammonium cations.

In particular, the following POM(s) or derivatives thereof were found to be useful:
  potassium 11-tungstosilicate ($K_8[SiW_{11}O_{39}]$),
  vinylsilane hybrid of tungstosilicate ($K_4[SiW_{11}O_{40}(SiC_2H_3)_2]$),
  phenylsilane hybrid of tungstosilicate ($K_4[SiW_{11}O_{40}(SiC_6H_5)_2]$),
  butylsilane hybrid of tungstosilicate ($K_4[SiW_{11}O_{40}(SiC_4H_9)_2]$),
  gamma-methacryloxypropyltrimethoxysilane hybrid of 11-tungstosilicate ($K_4[SiW_{11}O_{40}(SiC_7H_{11}O_2)_2]$),
  lithium 6-molybdoaluminate $Li_3[Al(OH)_6Mo_6O_{18}]$
  2-(dimethylamino)ethyl acrylate salt of 12-tungstophosphoric acid (($H_2C{=}CHCO_2CH_2CH_2NH(CH_3)_2$)$_3$ $[PW_{12}O_{40}]$),
or mixtures thereof.

According to some embodiments, the POM cluster (e.g., dissolved POM cluster) can be characterized by at least one or all of the following parameters:
  Molecular size: from about 0.5 to about 5 nm;
  Molecular weight: from about 800 to about 10,000 g/mol;
  Structure: Keggin, Dawson, Lindquist or combination thereof;
  comprising an organic moiety;
  being water-soluble.

A molecular size within the above range can be beneficial in particular if a highly translucent material is desired. A molecular weight within the above range can be beneficial in particular if a low volatility is desired. Providing POM with organic moieties can be beneficial in particular if compatibility with an organic polymer matrix is desired.

POM particles can be characterized by at least one or more or all of the following features:
  Particle size: from about 5 nm to about 50 μm or from about 7.5 nm to about 25 μm or from about 10 nm to 10 μm;
  not being fully dissolved in the resin composition;
  density: from about 1 g/cm$^3$ to about 5 g/cm$^3$ or from about 1.5 g/cm$^3$ to about 2.5 g/cm$^3$;
  shape: cylindrical, platelet, spherical, prolate ellipsoid, oblate ellipsoid, needle-like, polyhedral or irregular.

The POM is typically present in the following amounts. The amount is given with respect to the weight of the whole composition.
  Lower limit: at least about 5 or at least about 7 or at least about 10 wt.-%;
  Upper limit: utmost about 50 or utmost about 35 or utmost about 25 wt.-%;
  Range: from about 5 to about 50 or from about 7 to about 35 or from about 10 to about 33 or from about 12 to about 30 or from about 13 to about 28 wt.-%.

If the amount of POM in the dental composition is too low, the dental composition is not sufficiently radiopaque. In some embodiments, the polyoxometalate(s) and/or derivatives thereof as described in the present text may be present within the dental composition in an amount sufficient to increase the radiopacity of the composition to a targeted level, based on a design goal for the composition to have radiopacity comparable to that of dentin (approximately 100% compared to an aluminum specimen of 1 mm thickness determined according to ISO 4049). Accordingly, in some embodiments, the polyoxometalate(s) and/or derivatives thereof as described in the present text may be present within the dental composition in an amount sufficient to increase the radiopacity of the composition to at least about 80% (in some embodiments at least about 90%, in some embodiments at least about 100%) compared to an aluminum specimen of 1 mm thickness determined according to ISO 4049. In some embodiments, the polyoxometalate(s) and/or derivatives thereof as described in the present text may be present within the dental composition in an amount sufficient to increase the radiopacity of the composition to between 80% and 150% (in some embodiments between 85% and 125%, in some embodiments between 90% and 110%, in some embodiments between 95% and 105%) compared to an aluminum specimen of 1 mm thickness determined according to ISO 4049. In some embodiments, the polyoxometalate(s) and/or derivatives thereof as described in the present text may be present within the dental composition in an amount sufficient to increase the radiopacity of the composition to a targeted level, based on a design goal for the composition to have radiopacity comparable to that of enamel (approximately 200% compared to an aluminum specimen of 1 mm thickness determined according to ISO 4049). Accordingly, in some embodiments, the polyoxometalate(s) and/or derivatives thereof as described in the present text may be present within the dental composition in an amount sufficient to increase the radiopacity of the composition to at least about 160% (in some embodiments at least about 180%, in some embodiments at least about 200%) compared to an aluminum specimen of 1 mm thickness determined according to ISO 4049. In some embodiments, the polyoxometalate(s) and/or derivatives thereof as described in the present text may be present within the dental composition in an amount sufficient to increase the radiopacity of the composition to between 160% and 240% (in some embodiments between 170% and 230%, in some embodiments between 180% and 220%, in some embodiments between 190% and 210%) compared to an aluminum specimen of 1 mm thickness determined according to ISO 4049. For polyoxometalate(s) and/or derivatives thereof as described in the present text to be present within the dental composition in an amount sufficient to increase the radiopacity of the composition to a specified level compared to an aluminum specimen of 1 mm thickness determined according to ISO 4049, what is meant is that the same dental composition without the polyoxometalate(s) and/or derivatives thereof exhibits radiopacity of a level that is lower than the specified level.

If the amount of POM in the dental composition is too high, the POM may interfere with the initiator system. This may result in an insufficient curing behaviour. If desired, the dental composition described in the present text may also contain particulate filler(s) as component (D). POM particles are not regarded as filler component (D).

Adding a filler can be beneficial e.g. for adjusting the rheological properties like viscosity. The content of the filler also typically influences the physical properties of the composition after hardening, like hardness or flexural strength. The chemical nature of the filler(s) is not particularly limited unless the intended purpose cannot be achieved. The size of the filler particles should be such that a homogeneous mixture with the hardenable component forming the resin matrix can be obtained.

The particle size of the filler may be in a range from about 0.001 to about 10 µm. The filler(s) typically comprise non acid reactive fillers. A non-acid reactive filler is a filler which does not undergo an acid/base reaction with an acid. Useful non acid reactive fillers include fumed silica, quartz, ground glasses, non-water-soluble fluorides such as $CaF_2$, silica gels such as silicic acid, in particular pyrogenic silicic acid and granulates thereof, cristobalite, calcium silicate, zirconium silicate, zeolites, including the molecular sieves, barium sulphate, yttrium fluoride.

Suitable fumed silicas include for example, products sold under the tradename Aerosil™ series OX-50, -130, -150, and -200, Aerosil R8200 available from Degussa AG, (Hanau, Germany), CAB-O-SIL™ M5 available from Cabot Corp (Tuscola, Ill.), and HDK types, e.g. HDK-H 2000, HDK H15; HDK H18, HDK $H_2O$ and HDK H30 available from Wacker.

The average surface area of the silica particles is preferably greater than about 15 $m^2$/g more preferably greater than about 30 $m^2$/g. Filler(s) which can also be used include nano-sized fillers such as nano-sized silica. Suitable nano-sized particles typically have a mean particle size in the range of about 5 to about 80 nm.

Preferred nano-sized silicas are commercially available from Nalco Chemical Co. (Naperville, Ill.) under the product designation NALCO COLLOIDAL SILICAS (for example, preferred silica particles can be obtained from using NALCO products 1040, 1042, 1050, 1060, 2327 and 2329), Nissan Chemical America Company, Houston, Tex. (for example, SNOWTEX-ZL, -OL, -O, -N, -C, -20L, -40, and -50); Admatechs Co., Ltd., Japan (for example, SX009-MIE, SX009-MIF, SC1050-MJM, and SC1050-MLV); Grace GmbH & Co. KG, Worms, Germany (for example, those available under the product designation LUDOX, e.g., P-W50, P-W30, P-X30, P-T40 and P-T40AS); Akzo Nobel Chemicals GmbH, Leverkusen, Germany (for example, those available under the product designation LEVASIL, e.g., 50/50%, 100/45%, 200/30%, 200 A/30%, 200/40%, 200 A/40%, 300/30% and 500/15%), and Bayer MaterialScience AG, Leverkusen, Germany (for example, those available under the product designation DISPERCOLL S, e.g., 5005, 4510, 4020 and 3030).

Surface-treating the nano-sized silica particles before loading into the dental material can provide a more stable dispersion in the resin. Preferably, the surface-treatment stabilizes the nano-sized particles so that the particles will be well dispersed in the hardenable resin and results in a substantially homogeneous composition. Furthermore, it is preferred that the silica be modified over at least a portion of its surface with a surface treatment agent so that the stabilized particle can copolymerize or otherwise react with the hardenable resin during curing.

Thus, the silica particles as well as other suitable non acid-reactive fillers can be treated with a resin-compatibilizing surface treatment agent. Particularly preferred surface treatment or surface modifying agents include silane treatment agents capable of polymerizing with a resin. Preferred silane treatment agent include gamma-methacryloxylpropyltrimethoxysilane, available commercially under the trade designation A-174, available commercially from Witco OSi Specialties (Danbury, Conn.) and gamma-glycidoxypropyltrimethoxy silane, a product available under the trade designation G6720, available from United Chemical Technologies (Bristol, Pa.).

Alternatively a combination of surface modifying agents can be useful, wherein at least one of the agents has a functional group co-polymerizable with a hardenable resin. For example, the polymerizing group can be ethylenically unsaturated or a cyclic function subject to ring opening polymerization. An ethylenically unsaturated polymerizing group can be, for example, an acrylate or methacrylate, or vinyl group. A cyclic functional group subject to ring opening polymerization generally contains a heteroatom such as oxygen, sulfur or nitrogen, and preferably is a 3-membered ring containing oxygen such as an epoxide. Other surface modifying agents which do not generally react with hardenable resins can be included to enhance dispersibility or rheological properties. Examples of silane of this type include, for example, alkyl or aryl polyethers, alkyl, hydroxy alkyl, hydroxy aryl, or amino alkyl functional silanes.

Besides an inorganic material the filler(s) can also be based on an organic material. Examples of suitable organic filler particles include filled or unfilled pulverized polycarbonates, poly(meth)acrylates, polyepoxides, and the like. If desired, the measurement of the particle size of the filler particles can be done with a TEM (transmission electron microscopy) method, whereby a population is analyzed to obtain an average particle diameter.

A preferred method for measuring the particle diameter can be described is as follows:

Samples approximately 80 nm thick are placed on 200 mesh copper grids with carbon stabilized formvar substrates (SPI Supplies—a division of Structure Probe, Inc., West Chester, Pa.). A transmission electron micrograph (TEM) is taken, using JEOL 200CX (JEOL, Ltd. of Akishima, Japan and sold by JEOL USA, Inc.) at 200 Kv. A population size of about 50-100 particles can be measured and an average diameter is determined.

The amount of filler to be used in the filler matrix usually depends on the purpose for which the composition should be used.

If present, the filler is typically present in the following amounts. The amount is given with respect to the weight of the whole composition.

Lower limit: at least about 1 wt-% or at least about 5 wt-% or at least about 10 wt-%.
Upper limit: utmost about 95 wt-% or utmost about 85 wt-% or utmost about 75 wt-%.
Range: from about 1 wt-% to about 95 wt-% or from about 5 wt-% to about 85 wt-%.

If the amount of filler is too low, mechanical strength of the cured composition might be too low for the intended application. If the amount of filler is too high, undesirable handling properties like too high viscosity, or poor wetting and penetration of a dental hard tissue might occur. If desired, the dental composition described in the present text may also contain solvent(s). Any solvent may be used which does not react appreciably with the other components of the composition. Adding a solvent can be beneficial for adjusting the viscosity of the composition. If the composition is to be used as a dental adhesive, the composition typically contains a solvent.

Examples of solvents include, but are not limited to water, linear, branched or cyclic, saturated or unsaturated alcohols, ketones, esters or mixtures of two or more of said type of solvents with 2 to 10 C atoms or mixtures thereof. Preferred alcoholic solvents include methanol, ethanol, iso-propanol and n-propanol.

Other suitable organic solvents are THF, acetone, methylethyl ketone, cyclohexanol, toluene, alkanes and acetic acid alkyl esters, in particular acetic acid ethyl ester.

If present, the solvent is typically present in the following amounts. The amount is given with respect to the weight of the whole composition.

Lower limit: at least about 0.1 wt-% or at least about 5 wt-% or at least about 10 wt-%;
Upper limit: utmost about 50 wt-% or utmost about 30 wt-% or utmost about 20 wt-%;
Range: from about 0.1 wt-% to about 50 wt-% or from about 5 wt-% to about 30 wt-%.

If the amount of solvent is too low, the viscosity of the composition might be too high, and wetting and penetration of dental hard tissue might be impaired.

If the amount of solvent is too high, the composition might be too dilute for forming adequate bond or mechanical strength.

Besides the above mentioned components, the dental composition described in the present text may further contain one, two or more of the following additives:

x-ray visible particles not being POM,
pigments,
photobleachable colorants,
fluoride release agents,
stabilizers,
retarders,
and mixtures thereof.

Suitable x-ray visible particles which may be present in addition to the POM already contained in the dental composition described in the present text include particles of metal oxides like the oxides of yttrium, ytterbium, strontium, barium, zirconium, hafnium, niobium, tantalum, tungsten, bismuth, molybdenum, tin, zinc, lanthanide elements (i.e. elements having atomic numbers ranging from 57 to 71, inclusive), cerium and combinations thereof. Most preferably, the oxides of heavy metals having an atomic number greater than 30, but less than 72 are optionally included in the materials of the invention. Particularly preferred radiopacifying metal oxides include lanthanum oxide, zinc oxide, tin oxide, zirconium oxide, yttrium oxide, ytterbium oxide, barium oxide, strontium oxide, cerium oxide, and combinations thereof.

Examples of pigments, which can be used include titanium dioxide or zinc sulphide (lithopones), red iron oxide 3395, Bayferrox 920 Z Yellow, Neazopon Blue 807 (copper phthalocyanine-based dye) or Helio Fast Yellow ER. These additives may be used for individual coloring of the dental compositions.

Examples of photobleachable colorants which can be present include Rose Bengal, Methylene Violet, Methylene Blue, Fluorescein, Eosin Yellow, Eosin Y, Ethyl Eosin, Eosin bluish, Eosin B, Erythrosin B, Erythrosin Yellowish Blend, Toluidine Blue, 4',5'-Dibromofluorescein and blends thereof. Further examples of photobleachable colorants can be found in U.S. Pat. No. 6,444,725. The color of the compositions of the invention may be additionally imparted by a sensitizing compound.

Examples of fluoride release agents which can be present include naturally occurring or synthetic fluoride minerals. These fluoride sources can optionally be treated with surface treatment agents.

Further additives, which can be added, include stabilizers, especially free radical scavengers such as substituted and/or unsubstituted hydroxyaromatics (e.g. butylated hydroxytoluene (BHT), hydroquinone, hydroquinone monomethyl ether (MEHQ), 3,5-di-tert-butyl-4-hydroxyanisole (2,6-di-tert-butyl-4-ethoxyphenol), 2,6-di-tert-butyl-4-(dimethylamino)methylphenol or 2,5-di-tert-butyl hydroquinone, 2-(2'-hydroxy-5'-methylphenyl)-2H-benzotriazole, 2-(2'-hydroxy-5'-t-octylphenyl)-2H-benzotriazole, 2-hydroxy-4-methoxybenzophenone (UV-9), 2-(2'-hydroxy-4',6'-di-tert-pentylphenyl)-2H-benzotriazole, 2-hydroxy-4-n-octoxybenzophenone, 2-(2'-hydroxy-5'-methacryloxyethylphenyl)-2H-benzotriazole, phenothiazine, and HALS (hindered amine light stabilizers).

Further additives, which can be added, include retarders, (such as 1,2-diphenylethylene), plasticizers (including polyethylene glycol derivatives, polypropylene glycols, low-molecular-weight polyesters, dibutyl, dioctyl, dinonyl and diphenyl phthalate, di(isononyl adipate), tricresyl phosphate, paraffin oils, glycerol triacetate, bisphenol A diacetate, ethoxylated bisphenol A diacetate, and silicone oils), flavorants, anti-microbials, fragrance, agents that impart fluorescence and/or opalescence and fluoride releasing materials.

There is no need for the additive(s) to be present, however, if present, the additive(s) is(are) typically present in the following amounts. The amount is given with respect to the weight of the whole composition.

Lower limit: at least about 0.01 wt-% or at least about 0.05 wt-% or at least about 0.1 wt-%;

Upper limit: utmost about 15 wt-% or utmost about 10 wt-% or utmost about 5 wt-%;

Range: from about 0.01 wt-% to about 15 wt-% or from about 0.01 wt-% to about 10 wt-%.

According to one embodiment, the dental composition described in the present text may contain the respective components in the following amounts (wt.-% with respect to the weight of the whole composition):

Resin Matrix (A): from about 10 to about 90 or from about 20 to about 80 wt.-%;

Initiator System (B): from about 0.1 to about 10 or from about 0.5 to about 5 wt.-%;

Polyoxymetalate (C): from about 1 to about 50 or from about 5 to about 30 wt.-%;

Filler (D): from about 1 to about 90 or from about 3 to about 80 wt.-%;

Solvent (E): from about 0 to about 50 or from about 5 to about 30 wt.-%;

Additive (F): from about 0.01 to about 15 or from about 0.05 to about 10 wt.-%.

In certain embodiments the dental composition fulfils at least one or more, sometimes all of the following properties (before hardening):

a) radiopacity: at least about 80% of the radiopacity of a 1 mm thick aluminum specimen, determined according to ISO 4049;

b) storage stable;

c) pH value: from about 0 to about 6;

d) viscosity: from about 0.01 to about 1,000 Pa*s measured at 23° C.;

e) bond strength to cut enamel and dentin (if the composition is used as an adhesive, self-adhesive liner or self-adhesive filling material): at least from about 2 to about 10 MPa, measured by the notched edge shear bond test, according to ISO FDIS 29022:2013.

In certain embodiments, the combination of the following features is sometimes desirable: (a), (b) and (c). If desired, the measurement(s) can be performed as set out below in the example section. Depending on the intended use, the viscosity of the composition is typically adjusted. If the composition is used as dental adhesive or fissure sealant, suitable viscosities include e.g. from about 0.05 to about 5 Pa*s or from about 0.1 to about 2 Pa*s (23° C.; shear rate: 100 l/s; measured with a cone/plate geometry CP25-1 using a Physica MCR 301 Rheometer, Anton Paar GmbH, Graz, Austria). If the composition is used as dental filling composite, suitable viscosities include e.g. from about 0.5 to about 200 Pa*s or from about 1 to about 100 Pa*s (23° C.; shear rate: 100 l/s; measured with a cone/plate geometry CP25-1 using a Physica MCR 301 rheometer, Anton Paar GmbH, Graz, Austria).

According to one embodiment, the composition, if dissolved or dispersed in water (e.g. 1 g in 10 ml) typically exhibits a pH value in the range from about 0 to about 6 or from about 1 to about 4. That is, the composition as a whole may be acidic. The invention provides a composition which can be hardened in an acceptable time frame, e.g., less than about 300 seconds (s) or less than about 180 s or less than about 120 s, and to a sufficient depth using visible light source equipment already available in the dental office or electronics fabrication facilities.

In certain embodiments the dental composition fulfils at least one or more, sometimes all of the following properties (after hardening):

adhesion to dentin determined according to ISO 29022:2013: at least about 5 MPa or at least about 7 or at least about 9 MPa, adhesion to enamel determined according to wire ISO 29022:2013: at least about 7 MPa or at least about 9 or at least about 11 MPa.

The composition described in the present text is used in the dental field as a dental material or composition.

Such dental materials include direct aesthetic restorative materials (e.g., anterior and posterior restoratives), prostheses, adhesives and primers for oral hard tissues, sealants, veneers, cavity liners, orthodontic bracket adhesives for use with any type of bracket (such as metal, plastic and ceramic), crown and bridge cements, artificial crowns, artificial teeth, dentures, and the like.

These dental materials are used in the mouth and are disposed adjacent to natural teeth. The phrase "disposed adjacent to" as used herein refers to the placing of a dental material in temporary or permanent bonding (e.g., adhesive) or touching (e.g., occlusal or proximal) contact with a natural tooth. The term "composite" as used herein in the context of a dental material refers to a filled dental material. The term "restorative" as used herein refers to a dental composite that is polymerized after it is disposed adjacent to a tooth. The term "prosthesis" as used herein refers to a composite that is shaped and polymerized for its final use (e.g., as a crown, bridge, veneer, inlay, onlay or the like) before it is disposed adjacent to a tooth. The term "sealant" as used herein refers to a lightly filled dental composite or to an unfilled dental material that is cured after it is disposed adjacent to a tooth.

As used herein "adhesive" or "dental adhesive" refers to a composition used as a pre-treatment on a dental structure (e.g., a tooth) to adhere a "dental material" (e.g., "restorative" an orthodontic appliance (e.g., bracket), or an "orthodontic adhesive") to a dental surface. An "orthodontic adhesive" refers to a composition used to adhere an orthodontic appliance to a dental (e.g., tooth) surface. Generally, the dental surface is pre-treated, e.g., by etching, priming, and/or applying an adhesive to enhance the adhesion of the "orthodontic adhesive" to the dental surface.

The invention is also directed to a process for producing the composition as described in the present text, the process comprising the step of combining or mixing the polyoxymetalate with a resin matrix and an initiator system as described in the present text. The production process is preferably carried out under "safe light" conditions. Suitable means for mixing include speed mixers, dissolvers or kneaders. Suitable inert solvents may be employed if desired when producing the composition. Any solvent may be used which does not react appreciably with the components of the compositions. Examples of suitable solvents are those described above.

The inventive dental composition is typically stored in a container until use. Depending on the formulation, various containers can be used. The composition can be provided in the form of a one-component system or as a two-component system. This typically depends on the initiator system chosen. As the composition is radiation curable, it is usually provided as a one-component system.

If the dental composition is provided as a high viscous material and as a one-component system, it can be stored in a container having only one chamber such as a compule. The compule has typically a cylindrical housing with a front and a rear end and a nozzle. The rear end of the housing is usually sealed with a movable piston. Typically, the dental composition is dispensed out of the compule or container using an applier having a movable plunger (e.g. an application device having the shape of a caulk gun). Examples of suitable compules or containers are described in U.S. Pat. No. 5,624,260, EP 1 340 472 A1, US 2007/0172789 A1, U.S. Pat. No. 5,893,714 and U.S. Pat. No. 5,865,803, the content of which with regard to the description of compules or containers is herewith incorporated by reference. The composition may also be stored in a vessel or screw tube, a packaging form which is typically used for multiple applications.

Alternatively, if the dental composition is provided as a two-component system, it can be stored in a dual-chamber container or cartridge and is mixed before use. Cartridges which can be used are described e.g. in US 2007/0090079 or U.S. Pat. No. 5,918,772, the disclosure of which is incorporated by reference. Cartridges which can be used are commercially available from SulzerMixpac AG (Switzerland).

Static mixing tips which can be used are described e.g. in US 2006/0187752 or in U.S. Pat. No. 5,944,419, the disclosure of which is incorporated by reference. Mixing tips which can be used are commercially available from SulzerMixpac AG (Switzerland) The container may comprise a housing having a front end with a nozzle and a rear end and at least one piston movable in the housing.

Low viscous compositions can be stored in a vial or bottle. Suitable vials are described e.g. in EP 0 944 364 B1 and WO 2011/056814 A1. The content of these documents with respect to the description of the vial or bottle is herewith incorporated by reference. Low viscous composition may also be stored in a container formed by two sheets, interconnected by hot sealing and cooperating to form a compartment for receiving the liquid and a pocket for receiving a brush. These kind of devices are described e.g. in U.S. Pat. No. 6,105,761.

The volume of the container is typically in the range from about 0.1 to about 100 ml or from about 0.5 to about 50 ml or from about 1 to about 30 ml.

The dental composition described in the present text can be applied to the surface of hard dental tissue and cured e.g. by applying radiation.

A typical application process for the composition described in the present text typically includes the following steps in the desired order:
  providing the composition,
  placing the composition in contact with hard dental tissue, especially the surface thereof,
  curing the composition, e.g. by applying radiation (e.g. visible light) to the composition for a period of time sufficient to initiate the polymerisation process (e.g. about 5 to about 20 s).

If the composition is provided as a self-adhesive composition, no prior etching step or use of a bonding/primer is typically needed. Suitable tools for applying radiation include dental curing lights. Suitable dental curing lights are described e.g. in US 2005/0236586. The content of this document is herewith incorporated by reference. Suitable dental curing lights are also commercially available e.g. under the trade names Elipar™ S10 (3M ESPE).

Further embodiments of the invention described in the present text are given below:

Embodiment 1

According to one embodiment, the dental composition described in the present text comprises a curable resin, an initiator not being POM based, and dissolved POM clusters(s) comprising POM anion(s) and counter-cation(s), the POM anion(s) comprising organic group(s) covalently attached to the surface of POM cluster(s).

Embodiment 2

According to one embodiment, the dental composition described in the present text comprises a curable resin, an initiator not being POM based, dissolved POM cluster(s) comprising POM anion(s) and counter-cation(s), the counter-cation(s) comprising a polymerizable group.

Embodiment 3

According to one embodiment, the dental composition described in the present text comprises a curable resin, an initiator not being POM based, dissolved POM cluster(s) comprising POM anion(s) and counter-cation(s), the counter-cation(s) being attached to or part of a polymer.

Embodiment 4

According to one embodiment, the dental composition described in the present text is characterized as follows:
  Resin Matrix (A) in an amount from about 40 wt-% to about 80 wt-%;
  the resin matrix comprising hardenable components with one or more acidic moieties as component (A1) and components without acidic moieties as component (A2), component (A1) comprising a (meth)acrylate functionalized polyalkenoic acid;
  Initiator System (B) in an amount from about 0.5 wt-% to about 5 wt-%;
  the initiator comprising an iodonium salt or an acylphosphine oxide moiety but not champhorquinone (as an example for a 1,2 diketone component);
  Polyoxymetalate (C) in an amount from about 5 wt-% to about 25 wt-%;
  the POM comprising a moiety selected from $Li_3[Al(OH)_6Mo_6O_{18}]$, $K_4[SiW_{11}O_{40}(SiC_4H_9)_2]$, $K_4[SiW_{11}O_{40}(SiC_6H_5)_2]$, $(K_8[SiW_{11}O_{39}])$, $((H_2C{=}CHCO_2CH_2CH_2NH(CH_3)_2)_3[PW_{12}O_{40}])_5$ or mixtures thereof;
  Filler (D) in an amount from about 0 wt-% to about 20 wt-%;

the filler being selected from nanosilica, fumed silica, ground glass or mixtures thereof; with the filler being surface treated with a silane coupling agent;

Solvent (E) in an amount from about 5 wt-% to about 50 wt-%;

the solvent being selected from water, alcohols or mixtures thereof.

Embodiment 5

A curable dental composition for dental use comprising
a resin matrix comprising combinations of hardenable components with an acidic moiety and hardenable components without an acidic moiety as described in the present text,
an initiator system suitable for curing the hardenable components as described in the present text,
polyoxometalate(s) and/or derivatives thereof as described in the present text being present in an amount of at least about 5 wt.-% with respect to the weight of the composition.

Embodiment 6

A curable dental composition for dental use comprising
a resin matrix comprising hardenable components as described in the present text,
an initiator system comprising components comprising an acyl phosphine moiety, bisacylphosphine oxide, or combinations thereof for curing the hardenable components as described in the present text,
polyoxometalate(s) and/or derivatives thereof as described in the present text being present in an amount of at least about 5 wt.-% with respect to the weight of the composition.

Embodiment 7

A curable dental composition for dental use comprising
a resin matrix comprising hardenable components as described in the present text,
an initiator system suitable for curing the hardenable components as described in the present text,
polyoxometalate(s) and/or derivatives thereof as described in the present text being present in an amount sufficient to increase the radiopacity of the composition to at least about 80% compared to an aluminum specimen of 1 mm thickness determined according to ISO 4049.

Embodiment 8

A curable dental composition for dental use comprising
a resin matrix comprising hardenable components as described in the present text,
an initiator system suitable for curing the hardenable components as described in the present text,
polyoxometalate(s) and/or derivatives thereof as described in the present text without a polymerizable group covalently attached to the cluster being present in an amount of at least about 5 wt.-% with respect to the weight of the composition.

Using POM(s) and/or derivatives thereof without a polymerizable group covalently attached to the cluster may be beneficial, as the likelihood that an undesired reaction occurs, which may result in the formation of an insoluble POM additive, is reduced.

Embodiment 9

A curable dental composition for dental use comprising
a resin matrix comprising hardenable components as described in the present text,
an initiator system suitable for curing the hardenable components as described in the present text, the initiator system not comprising camphorquinone,
polyoxometalate(s) and/or derivatives thereof as described in the present text being present in an amount of at least about 5 wt.-% with respect to the weight of the composition.

Such a composition may be beneficial, if colouring effects of the composition during or after curing should be avoided.

All components used in the dental composition described in the present text should be sufficiently biocompatible, that is, the composition should not produce a toxic, injurious, or immunological response in living tissue.

In some embodiments, the dental composition does not contain one, more or all of the following components:
Nanosized zirconia in an amount above 5, 3, 1 or 0.5 wt.-%,
acid-reactive fillers in an amount above 5, 3, 1 or 0.5 wt.-%,
halogenated solvents,
tertiary amines containing an aromatic substituent attached to the N-atom of the amine moiety like 4-(N,N-dimethylamino)-benzoic acid ethyl ester, methyl 4-N,N-dimethylaminobenzoate, propyl 4-N,N-dimethylaminobenzoate, n-butoxyethyl 4-N,N-dimethylaminobenzoate, 2-(methacryloyloxy)ethyl 4-N,N-dimethylaminobenzoate and 4-N,N-dimethylaminobenzophenone,
camphorquinone,
zirconium clusters comprising a polymerizable group;
(wt.-% with respect to the amount of the whole compositions).

In some embodiments, the dental composition is essentially or substantially free of or does not contain any of the above components at all.

The complete disclosures of the patents, patent documents, and publications cited herein are incorporated by reference in their entirety as if each were individually incorporated. Various modifications and alterations to this invention will become apparent to those skilled in the art without departing from the scope and spirit of this invention. The above specification, examples and data provide a description of the manufacture and use of the compositions and methods of the invention. The invention is not limited to the embodiments disclosed herein. One skilled in the art will appreciate that many alternative embodiments of the invention can be made without departing from the spirit and scope of thereof.

Examples

The following examples are given to illustrate the invention.

Unless otherwise indicated, all parts and percentages are on a weight basis, all water is de-ionized water, and all molecular weights are weight average molecular weight. Moreover, unless otherwise indicated all experiments were conducted at ambient conditions (23° C.; 1013 mbar). All percentages given are weight-%.

Measurements

Radiopacity

Radiopacity was measured using a Heliodent Plus dental X-ray device (Sirona, X-ray tube voltage: 60 kV, exposure time: 0.06 s). Radiopacity is given in percent of the radiopacity of a 1 mm thick aluminum plate.

Viscosity

If desired, the viscosity can be determined as follows: The viscosity can be measured using a Physica MCR 301 Rheometer (Anton Paar, Graz, Austria) with a cone/plate geometry CP25-1 under controlled shear rate at 23° C. The diameter is 25 mm, the cone angle 1°, and the separation between the cone tip and the plate 49 μm. The shear rate is ramped down logarithmically from 1000 $s^{-1}$ to 1 $s^{-1}$, with a total of 23 data points being collected. The integration time for each data point was 10 s.

Storage Stability

If desired, storage stability can be determined as follows: The composition can be stored at elevated temperatures and/or different ambient humidity levels in the intended packaging. At certain time intervals, characteristic features such as adhesion, visual appearance, or mechanical strength can be determined.

pH Value

The pH value was determined as follows: A drop of the composition was placed on a flat glass slide. The pH was measured by exposing a flat electrode (Vario pH, WTW, Weilheim, Germany) to the drop until the read-out was constant.

Adhesion

If desired, the adhesion to dentin or enamel can be determined according to ISO 29022:2013.

Abbreviations

HSiW12—12-tungstosilicic acid ($H_4[SiW_{12}O_{40}]$)
HEMA—2-hydroxyethyl methacrylate
PEG-400 DMA—polyethyleneglycol dimethacrylate, average molecular weight: 400
CPQ—camphorquinone
EDMAB—ethyl 4-dimethylaminobenzoate
DPIHFP—diphenyliodonium hexafluorophosphate
EDMOA—ethyl dimethoxyanthracene
BisGMA—bisphenol A diglycidyl methacrylate
MDP—reaction products of methacrylic acid with 1,10-decanediol and phosphorous oxide ($P_2O_5$)
DMAEMA—2-dimethylaminoethyl methacrylate
BHT—butylated hydroxytoluene
Lucirin™ TPO—diphenyl 2,4,6-trimethylbenzoylphosphine oxide
Butyl BAP—4-butylphenyl bis(2,6-dichlorobenzoyl)phosphine oxide
VBCP—Vitrebond™ Copolymer; prepared according to Example 11 of U.S. Pat. No. 5,130,347 (Mitra)
A200—Aerosil™ 200 fumed silica
MPS—methacryloxypropyl trimethoxysilane
POM Synthesis The following POMs were prepared:

The phenylsilane hybrid of tungstosilicate ($K_4[SiW_{11}O_{40}(SiC_6H_5)_2]$) was synthesized as described in "Derivatives of Heteropolyanions. 1. Organic Derivatives of $W_{12}SiO_{40}^{4-}$, $W_{12}PO_{40}^{3-}$, and $Mo_{12}SiO_{40}^{4-}$"; J. Amer. Chem. Soc. 1979, 100, 759-760.

The butylsilane hybrid of tungstosilicate ($K_4[SiW_{11}O_{40}(SiC_4H_9)_2]$) was synthesized according to the following procedure:

To a solution of acetonitrile (40 mL) and distilled water (12 mL) was added $K_8[SiW_{11}O_{39}]\cdot13\ H_2O$ (5.00 g, 1.55 mmol) under vigorous stirring. This mixture was stirred for 10 min and then butyltrimethoxysilane (0.6 mL, 3.1 mmol) was added. The reaction mixture was stirred another 10 min and to this was added concentrated HCl (0.77 mL, 9.3 mmol) dropwise via syringe. The flask was capped and allowed to stir at room temperature overnight. A small amount of white precipitate was removed by filtration giving a clear, colorless solution. The solvent was then removed by rotary evaporation and then under high vacuum. A white solid resulted with the molecular formula $K_4[SiW_{11}O_{40}(SiC_4H_9)_2]$ and was characterized by IR, MALDI-TOF, and NMR spectroscopy.

The gamma-methacryloxypropyltrimethoxysilane hybrid of 11-tungstosilicate ($K_4[SiW_{11}O_{40}(SiC_7H_{11}O_2)_2]$) can be synthesized according to the following procedure: To a solution of acetonitrile (40 mL) and distilled water (12 mL) was added $K_8[SiW_{11}O_{39}]\cdot13\ H_2O$ (5.00 g, 1.55 mmol) under vigorous stirring. This mixture was stirred for 5 min and then gamma-methacryloxypropyltrimethoxysilane (0.74 mL, 3.1 mmol) was added. The reaction mixture was stirred another 10 min and to this was added concentrated HCl (0.77 mL, 9.3 mmol) dropwise via syringe. The flask was capped and allowed to stir at room temperature overnight. A small amount of precipitate was removed by filtration giving a clear, colorless solution. The solvent was then removed by rotary evaporation at ambient temperature and then under high vacuum overnight. A light yellow solid resulted with the molecular formula $K_4[SiW_{11}O_{40}(SiC_7H_{11}O_2)_2]$ and was characterized by IR, MALDI-TOF, and NMR spectroscopy.

The counter cations (i.e. $NH_4$, K) of the heteropoly complexes can be ion exchanged for Li to give compounds that were more soluble in the formulation.

An ion exchange can be accomplished as follows: A column (1.25" diameter) was loaded with Dowex-50W 100-200 dry mesh in the hydrogen form to a height of 11". This was first eluted with distilled water until a pH of approximately 5 was reached. This was then eluted with 2M LiCl aqueous solution which initially caused the pH to drop. Elution was continued until the pH approached neutral (5-6) and then elution was continued with distilled water to remove excess LiCl (1000 mL).

As an example of ion exchange with a heteropoly complex, the column was loaded with a 10 mL suspension of $(NH_4)_3[Al(OH)_6Mo_6O_{18}]$ (2 g) and was eluted with 500 mL of distilled water. As the water eluted the solid in the suspension at the top of the column dissolved. The eluent was collected and concentrated by rotary evaporation to give a white solid which was dried under high vacuum ($Li_3[Al(OH)_6Mo_6O_{18}]$, 1.75 g). The compound was characterized by MALDI-TOF analysis.

The 2-(dimethylamino)ethyl acrylate salt of 12-tungstophosphoric acid (($H_2C\!\!=\!\!CHCO_2CH_2CH_2NH(CH_3)_2)_3[PW_{12}O_{40}]$) was synthesized as follows:

The 12-tungstophosphoric acid (2.0 g, 0.65 mmol) was loaded into a vial and dissolved in distilled water (5 mL). To this solution 2-(dimethylamino)ethyl acrylate (0.30 mL, 1.9 mmol) was added drop-wise via syringe. A white precipitate immediately formed and the reaction mixture was magnetically stirred for 1 h. The precipitate was collected by filtration and rinsed with water (2×3 mL). This was allowed to dry overnight to give a white solid (1.24 g). The compound was characterized by $^1$H, $^{13}$C, and $^{31}$P NMR spectroscopy and MALDI-TOF analysis.

Adhesive Formulations

The following formulations were prepared and cured with a dental curing light (Elipar™ Trilight; 3M ESPE; 3M Deutschland GmbH). The cured adhesives were visually inspected for their appearance and tested with respect to a variety of properties.

| | ADH-XTE-0125 | ADH-XTE-0126 | Comparative Example: ADH-XTE-0127 |
|---|---|---|---|
| Hardenable Component without acidic moiety | | | |
| BisGMA | 19.51% | 19.51% | 19.51% |
| HEMA | 23.41% | 23.41% | 23.41% |
| Solvent | | | |
| Ethanol | 13.19% | 13.19% | 13.19% |
| DI Water | 11.17% | 11.17% | 11.17% |
| Hardenable Component with acidic moiety | | | |
| MDP | 15.92% | 15.92% | 15.92% |
| VBCP | 2.04% | 2.04% | 2.04% |
| Initiator | | | |
| DMAEMA | 0.71% | 0.71% | 0.71% |
| BHT | 0.10% | 0.10% | 0.10% |
| CPQ | 1.62% | 1.62% | 1.62% |
| EDMAB | 1.02% | 1.02% | 1.02% |
| Lucirin™ TPO POM | 2.44% | 2.44% | 2.44% |
| Li3[Al(OH)6Mo6O18] | 8.87% | | |
| K4[SiW11O40(SiC4H9)2] | | 8.87% | |
| Silane treated nanozirconia filler prepared as in WO 2012/64573 A1 | | | 8.87% |
| Sum | 100.00% | 100.00% | 100.00% |
| pH | 3.72 | 2.62 | 3.54 |
| Radiopacity [%] | 109% | 118% | 71% |
| Handling after preparation | liquid | liquid | liquid |
| Handling after 1 week at 50° C. | liquid | liquid | gelled |
| Appearance (cured) | Blue | blue | Yellow |

To avoid blue colour formation, the following compositions were prepared.

| | ADH-XTE-0084 | ADH-XTE-0085 | ADH-XTE-0088 | ADH-XTE-0089 |
|---|---|---|---|---|
| Hardenable Component without acidic moiety | | | | |
| BisGMA | 18.05% | 18.16% | 15.86% | 15.63% |
| HEMA | 21.66% | 21.79% | 19.03% | 18.76% |
| Solvent | | | | |
| Ethanol | 12.20% | 12.27% | 10.72% | 10.56% |
| DI Water | 10.33% | 10.39% | 9.08% | 8.95% |
| Hardenable Component with acidic moiety | | | | |
| MDP | 14.76% | 14.84% | 12.77% | 12.78% |
| VBCP | 1.91% | 1.90% | 1.67% | 1.66% |
| Initiator | | | | |
| DMAEMA | 0.66% | 0.67% | 0.51% | 0.58% |
| BHT | 0.10% | 0.10% | 0.10% | 0.09% |
| Butyl BAP | 0.92% | 0.37% | 0.81% | |
| Lucirin™ TPO | | | | 1.87% |
| Filler | | | | |
| A200 | 7.51% | 7.55% | 6.55% | 6.50% |
| Additive | | | | |
| MPS | 2.81% | 2.88% | 2.40% | 2.60% |
| POM | | | | |
| K4 [SiW11O40(SiC4H9)2] | 9.09% | 9.09% | 20.51% | 20.01% |
| Sum | 100.00% | 100.00% | 100.00% | 100.00% |
| Curing light | LED | LED | LED | Halogen |
| Radiopacity | 106% | 109% | 228% | 223% |
| Appearance (cured) | clear | clear | clear | clear |

The invention claimed is:

1. A curable dental composition for dental use comprising:
    a resin matrix comprising hardenable components, the hardenable components comprising a hardenable component with at least one acidic moiety (A1) and a hardenable component without an acidic moiety (A2), wherein at least one of the hardenable components comprises two or more polymerizable groups, the resin matrix comprising from about 40 to about 80 wt.-% with respect to the weight of the composition;
    an initiator system suitable for curing the hardenable components, the initiator system comprising components comprising an acyl phosphine moiety, bisacylphosphine oxide, or combinations thereof, but not camphorquinone and the initiator system comprising from about 0.5 to about 5 wt.-% with respect to the weight of the composition
    polyoxometalate(s) and/or derivatives thereof being present in an amount from about 5 wt.-% to about 20 wt.-% with respect to the weight of the composition.

2. The composition of claim 1, wherein the polyoxometalate(s) is selected from dissolved polyoxometalate cluster(s), polyoxometalate particle(s) and combination(s) thereof.

3. The composition of claim 1, wherein the polyoxometalate(s) comprises a dissolved polyoxometalate cluster, wherein the dissolved polyoxometalate cluster is charge-balanced by a counter-cation, and wherein either the counter-cation or the polyoxometalate anion comprises an organic moiety which can comprise an unsaturated group.

4. The composition of claim 1, wherein the polyoxometalate comprises a dissolved polyoxometalate cluster(s), and wherein the dissolved polyoxometalate cluster(s) comprises polyoxometalate anion(s) being characterized by the formula $(X_xM_mM'_nO_y)^{q-}$, with X being selected from Cu, Zn, Co, Fe, B, Ga, Rh, Al, Cr, Mn, Ni, Ti, Zr, Si, Ge P, As, Te, I,
x being from about 0 to about 30,
m being from about 3 to about 248 and
n being from about 0 to about m/2,
y being from about 10 to about 720,
with the proviso that (0≤x<m+n),
M or M' being one or more transition metal,
O being oxygen,
q being from about 1 to about 20.

5. The composition of claim 1, further comprising the polyoxymetalate(s) as dissolved polyoxometalate cluster(s), the dissolved polyoxometalate cluster(s) being characterized by at least one or all of the following features:
molecular size: from about 0.5 to about 5 nm,
molecular weight: from about 800 to about 10,000 g/mol.

6. The composition of claim 1, wherein the hardenable component with at least one acidic moiety (A1) is characterized by the following formula:

$A_n\text{-}B\text{—}C_m$ with A being an ethylenically unsaturated group,
B being a spacer group selected from (i) linear or branched C1 to C12 alkyl, optionally substituted with halogen atoms and/or hydroxyl groups (ii) C6 to C12 aryl, optionally substituted with other functional groups with halogen atoms and/or hydroxyl groups, or (iii) organic group having 4 to 20 carbon atoms bonded to one another by one or more ether, thioether, ester, thioester, thiocarbonyl, amide, urethane, carbonyl and/or sulfonyl linkages,
C being an acidic moiety,
m, n being independently selected from 1, 2, 3, 4, 5 or 6, wherein the acidic moiety comprises one or more carboxylic acid residues, phosphoric acid residues, phosphonic acid residues, sulphonic acid residues, or sulfinic acid residues.

7. The composition of claim 1, wherein the hardenable component without an acidic moiety (A2) is characterized by the following formula:

$A_n\text{-}B\text{-}A_m$ with A being an ethylenically unsaturated group,
B being selected from (i) linear or branched C1 to C12 alkyl, optionally substituted with halogen atoms, and/or hydroxyl groups (ii) C6 to C12 aryl, optionally substituted with halogen atoms, and/or hydroxyl groups, or (iii) organic group having 4 to 20 carbon atoms bonded to one another by one or more ether, thioether, ester, thioester, thiocarbonyl, amide, urethane, carbonyl and/or sulfonyl linkages,
m, n being independently selected from 0, 1, 2, 3, 4, 5 or 6 with the proviso that n+m is greater 0.

8. The composition of claim 1, wherein the initiator system is capable of initiating polymerization via radiation, heat, electronic beam, or redox chemical reaction and combinations thereof.

9. The composition of claim 1 being characterized by at least one, two or all of the following parameters:
Radiopacity: at least about 80% compared to an aluminum specimen of 1 mm thickness determined according to ISO 4049,
Storage stable,
pH value: from about 0 to about 6,
Viscosity: from about 0.1 Pa*s to about 1,000 Pa*s measured at 23° C.

10. The composition of claim 1 not comprising components selected from nano-sized zirconia, acid-reactive filler or halogenated solvents or combinations thereof in amount above about 5 wt.-% with respect to the weight of the composition.

11. The composition of claim 1 for use as or for the production of a filling material, adhesive, sealant, primer, cavity liner, cement, artificial crowns, artificial teeth, veneer or denture.

* * * * *

UNITED STATES PATENT AND TRADEMARK OFFICE
CERTIFICATE OF CORRECTION

PATENT NO. : 10,028,894 B2
APPLICATION NO. : 14/917047
DATED : July 24, 2018
INVENTOR(S) : Adam Miller et al.

It is certified that error appears in the above-identified patent and that said Letters Patent is hereby corrected as shown below:

In the Specification

Column 1
Line 65, Delete "gellation" and insert -- gelation --, therefor.

Column 3
Line 7, Delete "Ge P," and insert -- Ge, P, --, therefor.

Column 3
Line 30, Delete "heterpolyoxometalate" and insert -- heteropolyoxometalate --, therefor.

Column 3
Lines 48-49, Delete "poloxometalate" and insert -- polyoxometalate --, therefor.

Column 6
Line 2, Delete "willfully" and insert -- wilfully --, therefor.

Column 7
Line 12, Delete "(i.e," and insert -- (i.e., --, therefor.

Column 9
Line 54, After "greater" insert -- than --.

Column 11
Line 19, Delete "($R^9$)$_2$P" and insert -- ($R^9$)$_2$—P --, therefor.

Column 12
Line 2, Delete "napthylphosphine" and insert -- naphthylphosphine --, therefor.

Signed and Sealed this
Sixteenth Day of April, 2019

Andrei Iancu
*Director of the United States Patent and Trademark Office*

Column 12
Line 14, Delete "oxide." and insert -- oxide, --, therefor.

Column 12
Line 61, Delete "photoinitator" and insert -- photoinitiator --, therefor.

Column 12
Line 63, Delete "(ie.," and insert -- (i.e., --, therefor.

Column 14
Line 36, Delete "photointiators" and insert -- photoinitiators --, therefor.

Column 15
Line 36, Delete "2-dimethylamino ethanol," and insert -- 2-dimethylaminoethanol, --, therefor.

Column 16
Line 66, Delete "[(methacryloyloxethyl)" and insert -- [(methacryloyloxyethyl) --, therefor.

Column 17
Line 30, Delete "give" and insert -- given --, therefor.

Column 17
Line 34, Delete "guanadinium" and insert -- guanidinium --, therefor.

Column 20
Line 13, Delete "$H_2O$" and insert -- H20 --, therefor.

Column 22
Line 37, Delete "Neazopon" and insert -- Neozapon --, therefor.

Column 23
Line 62, Delete "l/s;" and insert -- 1/s; --, therefor.

Column 24
Line 1, Delete "l/s;" and insert -- 1/s; --, therefor.

Column 25
Line 42, Delete "(Switzerland)" and insert -- (Switzerland). --, therefor.

Column 26
Line 57, Delete "champhorquinone" and insert -- camphorquinone --, therefor.

Column 26
Line 57, Delete "champhorquinone" and insert -- camphorquinone --, therefor.

CERTIFICATE OF CORRECTION (continued)
U.S. Pat. No. 10,028,894 B2

Column 26
Line 64, Delete "$O_{40}])_5$" and insert -- $O_{40}])$, --, therefor.

Column 31
Line 31, Delete "Lucirin ™" and insert -- Lucirin™ --, therefor.

Column 32
Line 7 (approx.), Delete "Lucirin ™" and insert -- Lucirin™ --, therefor.

In the Claims

Column 32
Line 59, In Claim 4, delete "Ge P," and insert -- Ge, P, --, therefor.

Column 34
Line 11 (approx.), In Claim 7, after "greater" insert -- than --.